(12) United States Patent
Hogan et al.

(10) Patent No.: US 9,737,380 B2
(45) Date of Patent: Aug. 22, 2017

(54) COMPONENTS FOR USE WITH IMPLANTS AND RELATED METHODS

(71) Applicant: AETON MEDICAL LLC, Philadelphia, PA (US)

(72) Inventors: Stephen Hogan, Wilmington, DE (US); Anatoli Krivoruk, Philadelphia, PA (US); Roger S. Ranck, Ambler, PA (US)

(73) Assignee: AETON MEDICAL LLC, Pennsauken, NJ (US)

( * ) Notice: Subject to any disclaimer, the term of this patent is extended or adjusted under 35 U.S.C. 154(b) by 0 days.

(21) Appl. No.: 13/874,966

(22) Filed: May 1, 2013

(65) Prior Publication Data

US 2014/0193775 A1  Jul. 10, 2014

Related U.S. Application Data

(63) Continuation of application No. 12/371,563, filed on Feb. 13, 2009, now abandoned.

(51) Int. Cl.
*A61C 8/00* (2006.01)

(52) U.S. Cl.
CPC .......... *A61C 8/0062* (2013.01); *A61C 8/0001* (2013.01); *A61C 8/0016* (2013.01);
(Continued)

(58) Field of Classification Search
CPC ..... A61C 8/0048; A61C 8/005; A61C 8/0051; A61C 8/0056; A61C 8/0062; A61C 8/0069
(Continued)

(56) References Cited

U.S. PATENT DOCUMENTS 3,849,887 A   11/1974   Brainin
4,281,991 A   8/1981   Michl et al.
(Continued)

FOREIGN PATENT DOCUMENTS

DE   10333013 A1   2/2005
EP   0 438 984 A1   7/1991
(Continued)

OTHER PUBLICATIONS

Carol Murphy, DentalTown Magazine, Apr. 2002, pp. 10-18, see p. 14, line 7-9.
(Continued)

*Primary Examiner* — Ralph Lewis
(74) *Attorney, Agent, or Firm* — Jones Robb, PLLC

(57) ABSTRACT

A system for dental restorations may comprise an abutment comprising an implant engaging portion and a component supporting portion terminating in a coronal end of the abutment. The implant engaging portion may extend apically from the component supporting portion and may have an external surface feature configured to be received in mating engagement within an opening in a dental implant. The component supporting portion may comprise at least one first snap-fit retention feature disposed on an outer peripheral surface of the component supporting portion. The system may further comprise a temporary coping made from a material that permits chemical bonding of the temporary coping with a veneering material of a temporary tooth restoration. The temporary coping may comprise at least one second snap-fit retention feature configured for snap-fit engagement with the at least one first snap-fit retention feature of the abutment.

34 Claims, 13 Drawing Sheets

(52) U.S. Cl.
CPC .......... *A61C 8/0069* (2013.01); *A61C 8/0071* (2013.01); *A61C 8/0074* (2013.01)

(58) Field of Classification Search
USPC .................................................. 433/172–175
See application file for complete search history.

(56) References Cited

U.S. PATENT DOCUMENTS

| | | | |
|---|---|---|---|
| 4,575,340 A | 3/1986 | Lustig | |
| 4,622,011 A | 11/1986 | Malek | |
| 4,657,510 A | 4/1987 | Gittleman | |
| 4,681,542 A | 7/1987 | Baum | |
| 4,722,688 A | 2/1988 | Lonca | |
| 4,997,723 A * | 3/1991 | Tanaka | A61C 13/082 |
| | | | 420/507 |
| 5,106,299 A | 4/1992 | Ghalili | |
| 5,118,296 A | 6/1992 | Eldred | |
| 5,195,891 A | 3/1993 | Sulc | |
| 5,334,024 A | 8/1994 | Niznick | |
| 5,376,004 A | 12/1994 | Mena | |
| 5,417,570 A | 5/1995 | Zuest et al. | |
| 5,613,854 A | 3/1997 | Sweatt | |
| 5,674,073 A | 10/1997 | Ingber et al. | |
| 5,685,715 A | 11/1997 | Beaty et al. | |
| 5,759,036 A | 6/1998 | Hinds | |
| 5,762,500 A | 6/1998 | Lazarof | |
| 5,782,637 A | 7/1998 | Cosenza | |
| 5,782,918 A | 7/1998 | Klardie et al. | |
| 5,823,776 A | 10/1998 | Duerr et al. | |
| 5,829,981 A | 11/1998 | Ziegler | |
| 5,904,483 A | 5/1999 | Wade | |
| 5,947,736 A | 9/1999 | Behrend | |
| 6,048,203 A | 4/2000 | Rosenberg | |
| 6,068,478 A | 5/2000 | Grande et al. | |
| 6,068,479 A | 5/2000 | Kwan | |
| 6,083,004 A | 7/2000 | Misch et al. | |
| 6,142,782 A | 11/2000 | Lazarof | |
| 6,149,433 A | 11/2000 | Ziegler et al. | |
| 6,155,828 A | 12/2000 | Lazzara et al. | |
| 6,159,010 A | 12/2000 | Rogers | |
| D441,448 S | 5/2001 | Kumar | |
| 6,290,500 B1 | 9/2001 | Morgan et al. | |
| 6,299,447 B1 | 10/2001 | Zuest et al. | |
| 6,332,777 B1 | 12/2001 | Sutter | |
| 6,382,977 B1 | 5/2002 | Kumar | |
| 6,524,106 B1 | 2/2003 | Ziegler | |
| 6,540,514 B1 | 4/2003 | Falk et al. | |
| 6,592,370 B2 | 7/2003 | Morgan | |
| 6,644,969 B2 | 11/2003 | Kumar | |
| 6,726,480 B1 | 4/2004 | Sutter | |
| 6,769,913 B2 | 8/2004 | Hurson | |
| 6,951,460 B2 | 10/2005 | Halldin et al. | |
| 6,981,871 B2 | 1/2006 | Mullaly et al. | |
| 7,014,464 B2 | 3/2006 | Niznick | |
| 7,066,736 B2 | 6/2006 | Kumar et al. | |
| 7,114,952 B2 | 10/2006 | Morgan | |
| 7,137,816 B2 | 11/2006 | Gervais et al. | |
| 7,163,398 B2 | 1/2007 | Klardie et al. | |
| 7,204,692 B2 | 4/2007 | Klardie et al. | |
| 7,207,800 B1 | 4/2007 | Kwan | |
| 7,207,801 B2 | 4/2007 | Vogt et al. | |
| 7,281,924 B2 | 10/2007 | Ellison | |
| 7,300,284 B2 | 11/2007 | Linder | |
| 7,309,231 B2 | 12/2007 | Engman | |
| 7,338,286 B2 | 3/2008 | Porter et al. | |
| 7,632,095 B2 | 12/2009 | Ostman et al. | |
| 8,075,313 B2 | 12/2011 | Ranck et al. | |
| 8,936,468 B2 | 1/2015 | Ranck et al. | |
| 2001/0026913 A1 | 10/2001 | Xu et al. | |
| 2002/0177103 A1 | 11/2002 | Pelak | |
| 2003/0054319 A1 | 3/2003 | Gervais et al. | |
| 2003/0082499 A1 | 5/2003 | Halldin et al. | |
| 2003/0097906 A1 | 5/2003 | Shoher et al. | |
| 2003/0114553 A1 | 6/2003 | Karim et al. | |
| 2004/0101806 A1 | 5/2004 | Kumar et al. | |
| 2004/0101807 A1 | 5/2004 | Porter et al. | |
| 2004/0121287 A1 | 6/2004 | Morgan | |
| 2004/0241610 A1 | 12/2004 | Hurson | |
| 2005/0014108 A1 | 1/2005 | Wohrle et al. | |
| 2005/0136378 A1 | 6/2005 | Ennajimi et al. | |
| 2005/0202370 A1 | 9/2005 | Brajnovic | |
| 2006/0003290 A1 | 1/2006 | Niznick | |
| 2006/0121416 A1 | 6/2006 | Engman | |
| 2006/0147881 A1 | 7/2006 | Winter-Moore | |
| 2006/0172257 A1 | 8/2006 | Niznick | |
| 2006/0188844 A1 | 8/2006 | Dadi | |
| 2006/0204928 A1* | 9/2006 | Hurson | 433/173 |
| 2006/0228672 A1* | 10/2006 | Hurson | 433/173 |
| 2006/0246397 A1 | 11/2006 | Wolf | |
| 2006/0263747 A1 | 11/2006 | Hurson | |
| 2006/0286508 A1 | 12/2006 | Bassett et al. | |
| 2007/0015110 A1 | 1/2007 | Zhang et al. | |
| 2007/0031103 A1 | 2/2007 | Tinucci et al. | |
| 2007/0031793 A1* | 2/2007 | Casement et al. | 433/218 |
| 2007/0141535 A1 | 6/2007 | Baldissara | |
| 2007/0281278 A1 | 12/2007 | Jorneus et al. | |
| 2007/0281279 A1 | 12/2007 | Chander | |
| 2008/0032263 A1 | 2/2008 | Bondar | |
| 2008/0096168 A1 | 4/2008 | Schonenberger | |
| 2008/0176186 A1 | 7/2008 | Schaub | |
| 2008/0206709 A1 | 8/2008 | Lannan | |
| 2008/0233539 A1 | 9/2008 | Rossler et al. | |
| 2008/0241792 A1 | 10/2008 | Rossler et al. | |
| 2009/0032989 A1 | 2/2009 | Karim et al. | |
| 2009/0123888 A1 | 5/2009 | Rosenberg | |
| 2009/0123891 A1 | 5/2009 | Rosenberg | |
| 2009/0305195 A1 | 12/2009 | Jones et al. | |
| 2010/0151420 A1 | 6/2010 | Ranck | |
| 2010/0151423 A1 | 6/2010 | Ranck et al. | |
| 2010/0159417 A1* | 6/2010 | Whipple | A61C 8/0075 |
| | | | 433/172 |
| 2010/0184002 A1 | 7/2010 | Ranck et al. | |
| 2010/0209877 A1 | 8/2010 | Hogan et al. | |
| 2010/0285427 A1 | 11/2010 | Hung | |
| 2011/0306014 A1 | 12/2011 | Conte et al. | |
| 2012/0135370 A1 | 5/2012 | Ranck et al. | |
| 2014/0113247 A1 | 4/2014 | Ranck | |
| 2015/0182308 A1 | 7/2015 | Ranck et al. | |

FOREIGN PATENT DOCUMENTS

| | | |
|---|---|---|
| KR | 20-0306037 Y1 | 3/2003 |
| KR | 2003-0030549 | 4/2003 |
| KR | 10-0428934 B1 | 4/2004 |
| KR | 10-0693806 B1 | 5/2006 |
| KR | 10-0799368 B1 | 1/2008 |
| WO | WO 03/030768 A1 | 4/2003 |
| WO | 03/049636 A1 | 6/2003 |
| WO | WO 2008/060565 A2 | 5/2008 |
| WO | WO 2008/093994 A1 | 8/2008 |
| WO | WO 2010/068552 A2 | 6/2010 |
| WO | WO 2010/068553 A2 | 6/2010 |
| WO | WO 2010/083393 A2 | 7/2010 |
| WO | WO 2010/093737 A2 | 8/2010 |
| WO | WO 2011/156668 A2 | 12/2011 |

OTHER PUBLICATIONS

International Search Report dated Aug. 25, 2010 for International Application No. PCT/US2009/066585.
Written Opinion of the International Search Authority dated Aug. 25, 2010 for International Application No. PCT/US2009/066585.
International Search Report dated Aug. 13, 2010 for International Application No. PCT/US2009/066584.
Written Opinion of the International Search Authority dated Aug. 13, 2010 for International Application No. PCT/US2009/066584.
International Search Report dated Sep. 30, 2010 for International Application No. PCT/US2010/021167.
Written Opinion of the International Search Authority dated Sep. 30, 2010 for International Application No. PCT/US2010/021167.
U.S. Office Action dated Oct. 13, 2010 for related U.S. Appl. No. 12/355,885.

(56) References Cited

OTHER PUBLICATIONS

International Search Report dated Nov. 11, 2010 for International Application No. PCT/US2010/023812.
Written Opinion of the International Search Authority dated Nov. 11, 2010 for International Application No. PCT/US2010/023812.
U.S. Office Action dated Jan. 4, 2011 for related U.S. Appl. No. 12/332,524.
Detailed bibliographic information from KIPRIS website for KR 2003-0030549.
U.S. Office Action dated Apr. 20, 2011 from related U.S. Appl. No. 12/355,885.
Response to Office Action dated Feb. 14, 2011 from related U.S. Appl. No. 12/355,885.
Response to Office Action dated Jul. 19, 2011 from related U.S. Appl. No. 12/355,885.
U.S. Office Action dated Jul. 14, 2011 from related U.S. Appl. No. 12/332,524.
Response to Office Action dated Jun. 6, 2011 from related U.S. Appl. No. 12/332,524.
"Protemp™ Plus Protemp™ Crown Temporization Material," brochure, 2009, 24 pp., 3M ESPE, St. Paul, USA.
Kim, S., DDS, PhD and Watts, D., PhD, DSc, "Degree of Conversion of Bis-Acrylic Based Provisional Crown and Fixed Partial Denture Materials," J Korean Acad Prosthodont, 2008, 5 pp., vol. 46, No. 6, Seoul, Korea.
Kurtzman, G., DDS, "Crown and Bridge Temporization Part 1: Provisional Materials," Inside Dentistry, 2008, 4 pp., vol. 8, Issue 8, AEGIS Communications, Newtown, USA.
Stannard, J., "Dental Sealant Selection and BPA (Bis-Phenol A)," [website page online]. Denali Corporation, [retrieved Sep. 8, 2011], Retrieved from the Internet: <http://dentalmaterialmatters.blogspot.com/2009/10/dental-sealant-selection-and-bpa-bis.html>.
Strassler, H., DMD, "In-Office Provisional Restorative Materials for Fixed Prosthodontics," Inside Dentistry, 2009, 7 pp., vol. 5, Issue 4, AEGIS Communications, Newtown, USA.
Oliva, G., "Mechanical Properties of Provisional Restorative Materials," thesis, 2010, 63 pp., Indiana University School of Dentistry, Indianapolis, USA.
Strassler, Howard, E., "Chairside Resin-Based Provisional Restorative Materials for Fixed Prosthodontics," 9 pp., [website page online]. CDE World, [retrieved Mar. 13, 2012], Retrieved from the Internet <http://cde.dentalaegis.com/courses/4552>.
McDonald, T., DMD, "Contemporary Temporization," brochure, 2009, 11 pp., ADA CERP Continuing Education Recognition Program.
Rueggeberg, Frederick A., "From vulcanite to vinyl, a history of resins in restorative dentistry," The Journal of Prosthetic Dentistry, Apr. 2002, pp. 364-379, vol. 87, No. 4.
International Search Report dated Feb. 27, 2012 for International Application No. PCT/US2011/039901.
Written Opinion of the International Search Authority dated Feb. 27, 2012 for International Application No. PCT/US2011/039901.
Response to Office Action dated Mar. 13, 2012 from related U.S. Appl. No. 12/332,524.
Office Action dated Mar. 21, 2012 from related U.S. Appl. No. 12/813,875.
"Protemp™ Plus Temporization Material," brochure, 2008, 4 pp., 3M ESPE, St. Paul, USA.
"Protemp™ Crown Temporization Material," brochure, 2007, 4 pp., 3M ESPE, St. Paul, USA.
"Protemp™ Plus Temporization Material," Technical Data Sheet, 2008, 6 pp., 3M ESPE, St. Paul, USA.
"The Direct Abutment," Astra Tech Implants, brochure, undated, 4 pp., Astra Tech Inc., Lexington, USA.
"Simple Solutions Prosthetic Technique Manual," Rev B Mar. 2008, 24 pp., BioHorizons USA, Birmingham, USA.
"Can You Prevail in the Pursuit of Crestal Bone Preservation?," Certain® PREVAIL® Implant System, brochure, Rev C 03/08, 8 pp., Biomet 3i™, Palm Beach Gardens, USA.

Östman, P., DDS, "NanoTite™ PREVAIL® Implants: Crestal Bone Preservation in the Aesthetic Zone," Clinical Perspectives, NanoTite™ Implant System, brochure, Jul. 2007, 7 pp., vol. 6, Issue 2, Biomet 3i™, Palm Beach Gardens, USA.
Lazzara, R. J., DMD, MScD, "Clinical Indications Demonstrating Bone Preservation with the Certain® PREVAIL® Implant," Clinical Indications, Certain® PREVAIL® Implant System, brochure, Rev A 2/07, 12 pp., Biomet 3i™, Palm Beach Gardens, USA.
"XP1 Transmucosal Implant System," [website page online]. Keystone Dental, Inc., [retrieved Mar. 3, 2009], Retrieved from the Internet: <URL: http://www.keystonedental.com/implants/xp1>.
"Cement-Retained Crowns and Bridges with the Solid Abutment System," catalog, Jan. 2008, 27 pp, Straumann, Basel, Switzerland.
"Immediate Temporary & QuickTemp™ Abutments—Temporary Solutions," catalog, 2007, 4 pp., Nobel Biocare Services AG.
"SPI®System—Design Concept," brochure, May 2005, 28 pp., Thommen Medical AG, Waldenburg, Switzerland.
"SPI®Easy—Prosthetic Procedure," brochure, Nov. 2006, 28 pp., Thommen Medical AG, Waldenburg, Switzerland.
"Restorative Manual," OSSEOTITE® Certain® Implant System and OSSEOTITE® External Hex Connection System, brochure, Rev B 11/07, 29 pp., Biomet 3i™, Palm Beach Gardens, USA.
"Basic Information on the Surgical Procedure," manual, Jan. 2007, 64 pp., Straumann, Basel, Switzerland.
"Basic Information on the Surgical Procedures," manual, Sep. 2007, 79 pp., Straumann, Basel, Switzerland.
Office Action dated Jan. 25, 2011 from corresponding U.S. Appl. No. 12/371,563.
Office Action dated Jul. 20, 2011 from corresponding U.S. Appl. No. 12/371,563.
Office Action dated Nov. 17, 2011 from corresponding U.S. Appl. No. 12/371,563.
Office Action dated Jul. 11, 2012 from corresponding U.S. Appl. No. 12/371,563.
Response dated May 24, 2011 from corresponding U.S. Appl. No. 12/371,563.
Response dated Oct. 20, 2011 from corresponding U.S. Appl. No. 12/371,563.
Response dated May 17, 2012 from corresponding U.S. Appl. No. 12/371,563.
Response dated Jul. 2, 2012 from corresponding U.S. Appl. No. 12/371,563.
Response dated Oct. 11, 2012 from corresponding U.S. Appl. No. 12/371,563.
Office Action dated Nov. 15, 2012 from related U.S. Appl. No. 12/332,524.
Office Action dated Jun. 22, 2012 from co-pending U.S. Appl. No. 13/299,503.
Office Action dated Feb. 26, 2013 from co-pending U.S. Appl. No. 13/299,503.
Office Action dated Jan. 21, 2014 from co-pending U.S. Appl. No. 13/299,503.
Notice of Allowance dated Sep. 12, 2014 from co-pending U.S. Appl. No. 13/299,503.
Response dated Oct. 22, 2012 from co-pending U.S. Appl. No. 13/299,503.
Response dated Jul. 26, 2013 from co-pending U.S. Appl. No. 13/299,503.
Response dated May 21, 2014 from co-pending U.S. Appl. No. 13/299,503.
Office Action dated May 6, 2014 from co-pending U.S. Appl. No. 13/874,976.
Response dated Oct. 6, 2014 from co-pending U.S. Appl. No. 13/874,976.
Cleveland, Cynthia M. et al, Fabrication of Provisional Crowns and Bridges, Received Nov. 6, 2012, http://www.dentalcare.com/en-US/dental-education/continuing-education/ce392/ce392.aspx?ModuleName=coursecontent&PartID=2&,SectionID=0.
Office Communication from related European Patent Application No. 10732140.8, dated Aug. 25, 2016.
Non-Final Office Action dated Apr. 9, 2015 from co-pending U.S. Appl. No. 13/874,976.

(56) References Cited

OTHER PUBLICATIONS

Final Office Action dated Nov. 20, 2015 from co-pending U.S. Appl. No. 13/874,976.
Response dated Aug. 10, 2015 from co-pending U.S. Appl. No. 13/874,976.
Extended European Search Report dated Sep. 4, 2015 for European Patent Application No. 10732140.8.

* cited by examiner

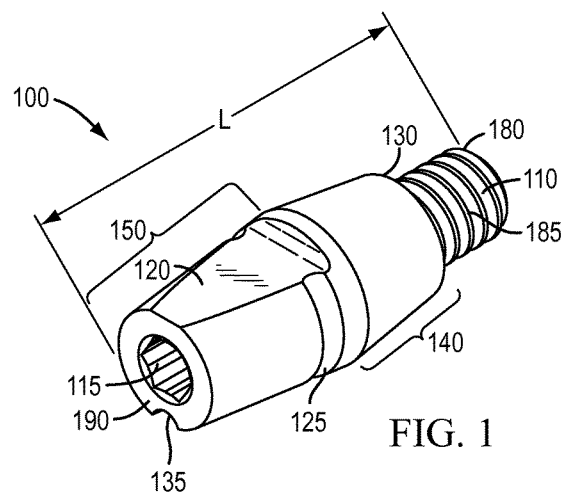
FIG. 1
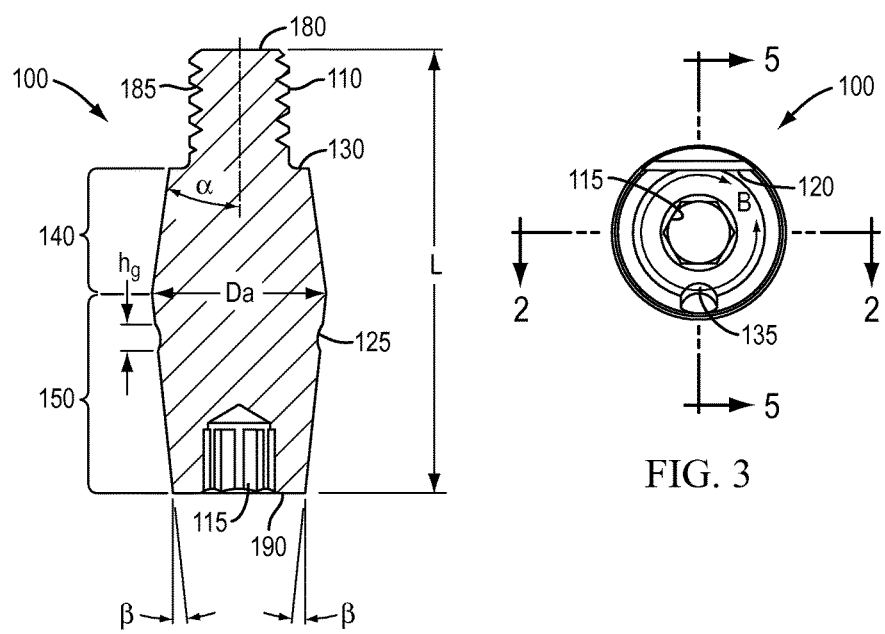
FIG. 2
FIG. 3

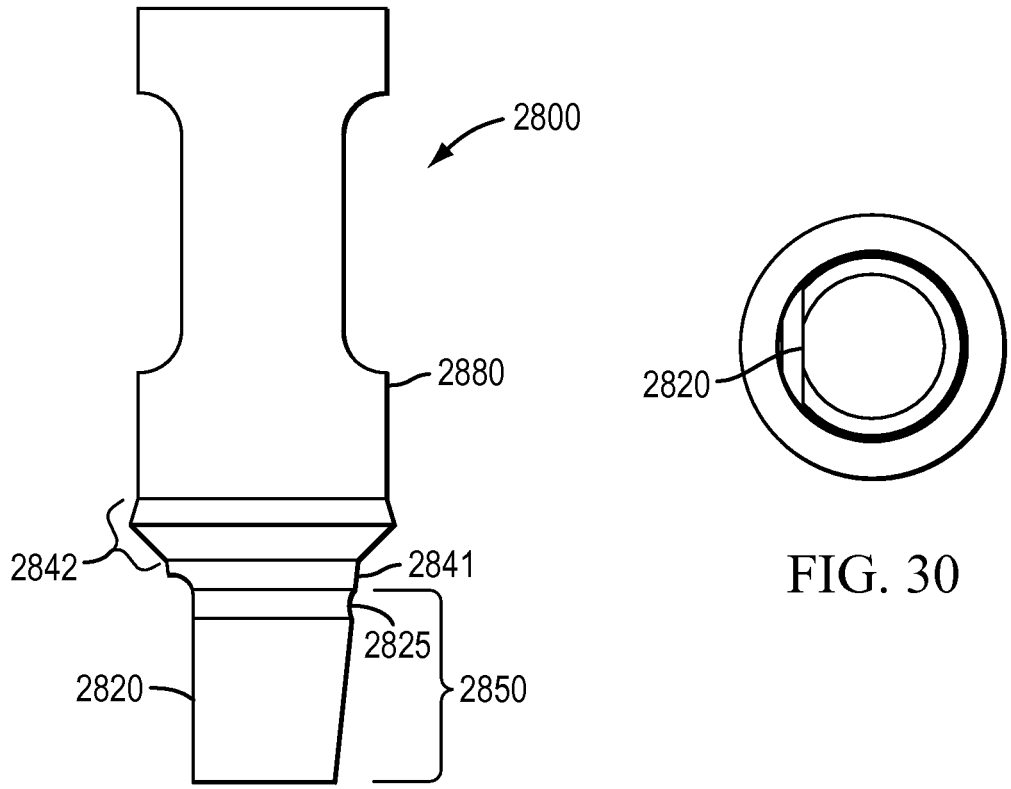
FIG. 28
FIG. 30
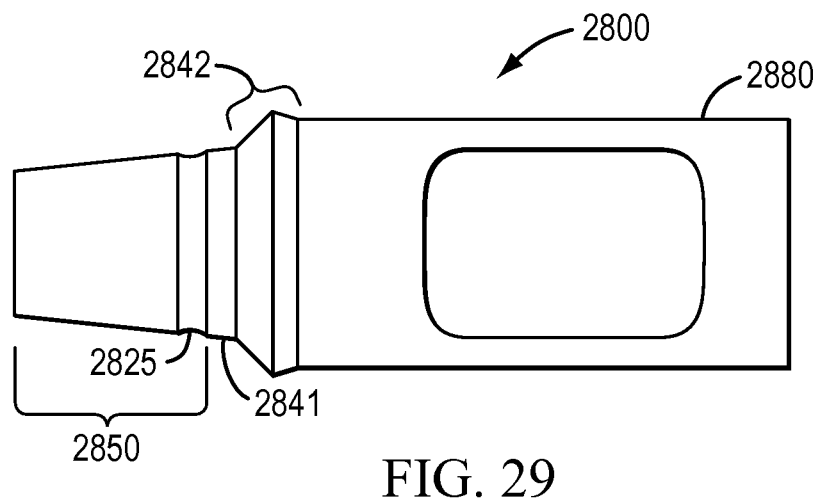
FIG. 29

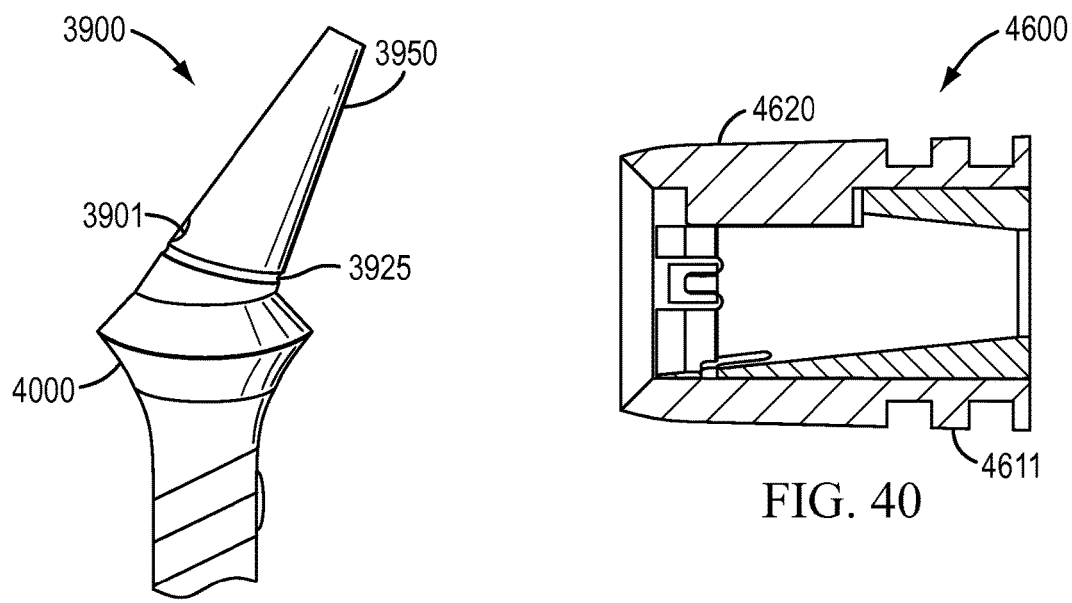
FIG. 39
FIG. 40
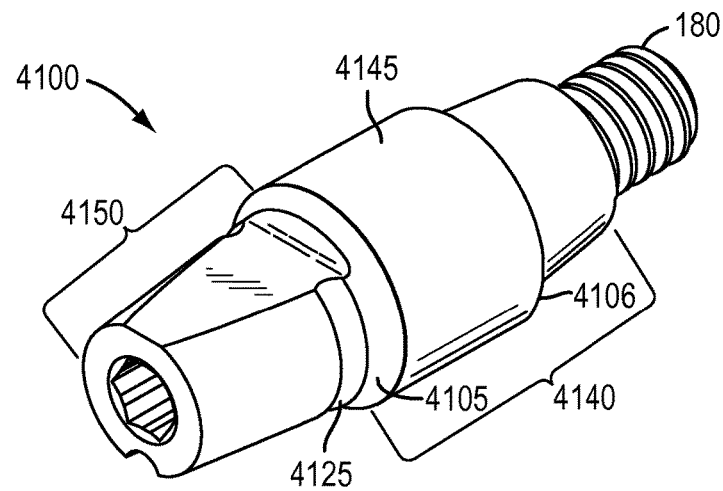
FIG. 41

COMPONENTS FOR USE WITH IMPLANTS AND RELATED METHODS

RELATED APPLICATION

This application is a continuation of U.S. patent application Ser. No. 12/371,563 (filed on Feb. 13, 2009; abandoned), the entirety of which is incorporated herein by reference.

TECHNICAL FIELD

The present teachings relate to components used with implants configured to be implanted in a patient's body, for example, in bone and/or cartilage. For example, the present teachings relate to components for taking an impression at the location of an implant fitted in the human body, transferring the impression to form a prosthetic part, and securing a prosthetic part to the implant. By way of particular example, the present teachings relate to components used with dental implants to make and secure to the implant temporary and/or permanent replacement teeth (restorations).

Introduction

Implants placed in bone and/or cartilage represent a growing field of reconstruction technology for replacing parts of the body, for example, with prosthetic parts. Such implants may be secured in the bone and/or cartilage and used to anchor a prosthetic body part in position. To facilitate making the prosthetic body part so as to ensure an accurate and aesthetically pleasing fit at the location of the implant, an impression of the implant's position implanted in the patient's body is taken to record the location and positioning of the implant, as well as parts of the body surrounding the implant.

One type of implant that has relatively widespread use includes dental implants. During dental implantation, a hole is drilled through the gingiva, the gums surrounding the root of a tooth, and/or into the jawbone. An implant, which may be, for example, made of titanium or titanium alloy, is then fixed within the hole of the jawbone. Over a period of months, the titanium implant fuses to the jawbone through a process called osseointegration. After a period of time, ranging from weeks to months, a permanent replacement tooth (sometimes referred to a final restoration or permanent restoration) is secured relative to the implant in the patient's mouth. Prior to placement of the permanent replacement tooth, a patient may also have a temporary replacement tooth (sometimes referred to as a temporary restoration) secured relative to the implant to provide some function and aesthetics in the time period before the permanent replacement tooth is in place.

Dental implant systems and techniques for making and implanting permanent and temporary replacement teeth generally involve the use of several component parts and steps. For preparing a permanent replacement tooth, one approach involves positioning an impression coping (also referred to as a transfer coping) relative to an implant fitted within the patient's mouth, embedding the impression coping in impression material to take an impression of the implant coronal end (i.e., the end which receives the restoration), any superstructure, such as, for example, an abutment, engaged with the implant, and the soft tissue and bone at the location of the implant, and transferring the so-formed impression to an analog (e.g., a replica of an abutment and shoulder portion of an implant) at a dental laboratory to produce a master cast by pouring modeling compound onto the impression.

At this stage, in one conventional technique, the impression coping with the impression material may be removed from the analog and master cast, and a plastic burnout coping may be positioned on the analog. Wax may be manipulated over the burnout coping to form the outline of a foundation which will ultimately be used to form a metal framework to which veneering material (such as, for example porcelain) is applied to form the permanent restoration. Once formed as desired, the wax and burnout coping are fit into a shell and molten metal is poured into the shell, burning out the wax and burnout coping, and upon solidifying, forming the metal framework. That process is sometimes referred to as a "lost wax" technique.

The metal framework is ultimately placed back on the analog and the veneer portion of the permanent restoration bonded thereto. The thus-formed permanent restoration structure can then be placed within the patient's mouth, with the framework being positioned over any superstructure on the implant (e.g., an abutment) and secured, for example, via cement, in position relative to the implant. When multiple replacement teeth are required, multiple burnout copings (e.g., two) may be placed on plural analogs and the procedure described above performed on each to create a metal framework that connects multiple permanent restorations together; those ordinarily skilled in the art are familiar with creating such frameworks for multiple permanent restorations.

For placing a temporary tooth, a so-called temporary coping is engaged with the implant, and, if any, superstructure, such as an abutment, in the patient's mouth and a material (such as, for example, an acrylic material) used to create a temporary tooth is bonded thereto. This process can be done either chairside by the dentist or in a dental laboratory. Some adjustments may be made to the height, angle, and/or inter-occlusal clearance of the portion of the abutment that supports the restoration if necessary, for example, by using a bur to shave the abutment. In some approaches, a plastic temporary coping designed to provide a mechanical bond, for example, via cement or other adhesive, with the veneering material may be placed over the abutment or a dental analog. Again, adjustments for inter-occlusal height, clearance, and/or angle of the temporary restoration may be made if necessary. Prefabricated polycarbonate crowns or vacuum stents may be used with a veneering material to complete fabrication of the temporary restoration.

To avoid tissue irritation, it is important to finish the interface between the temporary coping or framework and veneering material until it is smooth and the coping or framework is flush with the veneering material at the apical end of the restoration that mates with the implant. In some cases, as with the metal framework of the permanent restoration, any lip or other interfering feature on the temporary coping used to secure it onto implant, analog, or abutment is removed to provide a smooth interface and allow proper cementation and/or extrusion of excess cement. Temporary cement may then be used on the inner part of the temporary coping to secure it onto the abutment.

In some conventional impression techniques, the impression coping, as well as a temporary coping and/or a framework, is secured relative to the implant via a retention engagement with a shoulder of the dental implant. Such a configuration may pose problems when securing those components in position. For instance, since the implant may sit below the patient's gumline, it may be difficult to insert a coping that is configured to engage with the implant shoulder. Such difficulty includes knowing when proper engagement has occurred due to dampening of the sensation, e.g., tactile and/or auditory, of parts engaging beneath the gingival tissue. Moreover, it may be difficult to push the gingival tissue out of the way during engagement of a coping and/or framework with the implant, and thus can result in pinching a portion of the patient's gingival tissue. For example, for some conventional coping configurations that rely on a snap-fit retention between an end portion of the coping with the shoulder of the implant, a degree of expansion of the end of the coping may be required to achieve the snap-fit engagement. This may be difficult to achieve, especially when the location of engagement with the implant is too far below the gumline. In order to achieve the desired expansion, some conventional impression copings may be made of plastic and thus cannot be observed in an X-ray, potentially limiting the accuracy of the identification and impression of the location of the implant in the patient's mouth.

In addition, some conventional techniques rely on burnout coping configurations that include a mechanism, for example, substantially in the form of a lip disposed at a free end or other feature, configured to engage in a snap-on manner to the analog in the dental laboratory. Since the burnout coping is typically made of a deformable material, such as, for example, plastic, the lip relatively easily deforms to engage with the analog. A framework made from a mold that relies on such a burnout coping also has a corresponding lip disposed at its free end. However, due to the framework being made of a substantially non-deformable material (e.g., a metal or metal alloy), the framework may not be able to engage with the analog in a snap-on manner. Thus, in conventional techniques relying on such a burnout coping configuration, lips or other features on the framework are generally machined off to allow a flush mating with the analog, and thus the implant shoulder or abutment. Otherwise, the framework may not rest flush against the implant or abutment shoulder, once it is permanently mounted. Such improper fitting may create a space between the permanent restoration and the abutment and/or implant shoulder, which may produce wash-out of the bonding material (e.g., cement), damage (e.g., fracture) of the permanent restoration over time, and/or biological changes to tissue due to improper seating of the restoration.

Machining the framework may be time-consuming and also may result in an inaccurate fit between the permanent restoration and the analog and/or the abutment. Regarding the latter, because the lip that is machined off extends from a free end, determining how much of the lip to remove can be difficult. If not enough of the lip is removed, it may be difficult to achieve a flush mating (e.g., accurate seating). Too much removal off the permanent restoration framework may cause a gap between components. Although cement may fill some of those voids, cement may not provide the amount of mechanical strength that the metal cast does.

Also, in some conventional impression techniques, the analog in the dental laboratory is larger than the abutment on the implant, thereby resulting in a relatively loose fit between the permanent restoration and the abutment. Providing a looser fit (e.g., larger space) between the permanent restoration and the abutment may be necessary in order to allow room for the cement that is typically used to bond the permanent restoration relative to the implant. In other words, if not enough space is provided, excessive hydraulic pressures from the cement may occur when seating the permanent restoration, which could lead to inaccurate seating of the restoration upon hardening of the cement. Similar issues may arise for a temporary restoration since conventional temporary copings also are sized to provide a relatively loose fit between the temporary coping and the abutment to allow room for temporary cement used to bond the temporary restoration relative to the implant.

Based on some of the aforementioned issues, it may be desirable to provide a system that improves the accuracy and precision of the fit of a replacement tooth structure (whether a temporary or permanent restoration), e.g., with an abutment and implant, reduces the overall time spent on creating a restoration, and/or facilitates engaging a coping (such as, e.g., an impression and/or temporary coping) and/or framework of a permanent restoration relative to a dental implant, for example, to superstructure such as an abutment associated therewith, in a patient's mouth. To assist in achieving one or more of these desirable features, it further may be desirable to provide a burnout coping and/or analog from which to produce permanent restoration frameworks that provide a relatively tight and precise fit to an abutment/implant, rather than a looser fit provided when using some conventional techniques and their component parts. It also may be desirable to provide components, such as, for example, impression copings, temporary restorations and/or permanent restorations that are configured to provide a precise and sufficiently strong mechanical engagement with an abutment and that eliminate the need to use cement and/or other bonding material.

It also may be desirable to provide a dental impression and implant system that includes various components configured to engage with each other for use in taking impressions, making restorations, and securing restorations in a patient's mouth. It may be desirable to provide such components that are capable of engaging with existing dental implants with which dental professionals have familiarity.

SUMMARY

The present teachings may satisfy one or more of the above-mentioned desirable features and/or solve one or more of the above-mentioned problems. Other features and/or advantages may become apparent from the description that follows.

In accordance with various exemplary embodiments of the present teachings a system for taking an impression of an implant implanted in a patient's body may comprise an abutment comprising an implant engaging portion and a component supporting portion. The implant engaging portion may be configured to engage with an implant configured to be implanted in a patient's body and the component support portion may comprise at least one retention groove. The system may further comprise an impression coping configured to receive the component supporting portion and comprising at least one protrusion feature configured for snap-fit engagement with the at least one retention groove, wherein the impression coping is made from a material comprising metal.

In accordance with various exemplary embodiments of the present teachings, a system for replacing a body part with a prosthetic part may comprise an abutment comprising an implant engaging portion and a component supporting portion. The implant engaging portion may be configured to engage with an implant configured to be implanted in a patient and the component supporting portion comprising at least one retention groove. The system may further comprise a framework for a prosthetic part, the framework comprising at least one protrusion feature configured to engage with the at least one retention groove to retain the framework on the abutment.

In accordance with various exemplary embodiments of the present teachings, a kit for making and implanting dental restorations may comprise an abutment comprising an implant engaging portion and a component supporting portion. The implant engaging portion may be configured to engage with a dental implant and the component supporting portion may comprise at least one retention groove disposed on an outer peripheral surface of the component supporting portion. The kit may further comprise an impression coping comprising at least one protrusion feature configured for snap-fit engagement with the at least one retention groove, and a temporary coping comprising at least one protrusion feature configured for snap-fit engagement with the at least one retention groove.

In accordance with various exemplary embodiments of the present teachings, a method for taking an impression of an implant implanted in a patient's body may comprise snap-fitting at least one protrusion feature on an impression coping made of a material comprising metal to at least one retention groove disposed on an abutment attached to an implant implanted in a patient's body, placing impression material over at least a portion of the impression coping, and removing the impression coping together with the impression material placed over at least the portion of the impression coping from the abutment by lifting the impression coping from the abutment with a lifting force sufficient to disengage the at least one protrusion feature from the at least one retention groove.

In accordance with various exemplary embodiments of the present teachings, a method for implanting a permanent tooth restoration may comprise engaging at least one protrusion feature on a framework of a permanent tooth restoration with at least one retention groove disposed on an abutment attached to a dental implant implanted in a patient's body.

Additional objects and/or advantages of the present teachings will be set forth in part in the description which follows, and in part will be obvious from the description, or may be learned by practice of the present teachings. Those objects and advantages may be realized and attained by means of the elements and combinations particularly pointed out in the appended claims.

It is to be understood that both the foregoing general description and the following detailed description are exemplary and explanatory only and are not restrictive of the present teachings or claims. Rather, the claims are intended to cover a broad scope, including equivalents.

The accompanying drawings, which are incorporated in and constitute a part of this specification, illustrate exemplary embodiments of the present teachings and together with the description, serve to explain certain principles.

BRIEF DESCRIPTION OF THE DRAWINGS

FIG. 1 is a perspective view of an exemplary embodiment of an abutment in accordance with the present teachings;

FIG. 2 is a cross-sectional view of the abutment of FIG. 1 taken through line 2-2 of FIG. 3

FIG. 3 is a coronal end view of the abutment of FIG. 1;

FIG. 28 is a side view of an exemplary embodiment of an analog in accordance with the present teachings;

FIG. 29 is another side view of the analog of FIG. 28;

FIG. 30 is a coronal end view of the analog of FIG. 28;

FIG. 39 is a perspective view of an exemplary embodiment of an angled abutment in accordance with the present teachings;

FIG. 40 is a cross-sectional view similar to the view of FIG. 7 of another exemplary embodiment of an impression coping in accordance with the present teachings; and FIG. 41 is a perspective view of another exemplary embodiment of an abutment in accordance with the present teachings.

DETAILED DESCRIPTION OF VARIOUS EXEMPLARY EMBODIMENTS

Figure 4:
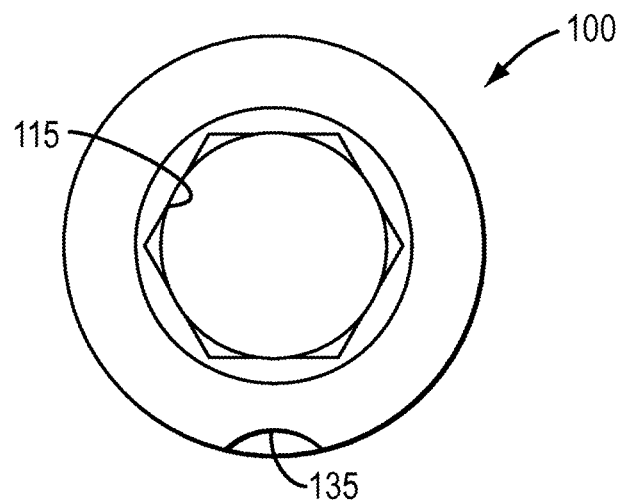
FIG. 4 shows a detailed view of section B in FIG. 3.

Reference will now be made in detail to various exemplary embodiments of the present teachings, examples of which are illustrated in the accompanying drawings. Wherever possible, the same reference numbers will be used throughout the drawings to refer to the same or like parts.

The present teachings contemplate systems and components thereof useful for taking dental impressions, creating replacement teeth (restorations), and securing restorations relative to a dental implant. It is contemplated that various exemplary embodiments of the present teachings may be used with impression techniques wherein an abutment is engaged with the implant at the time of taking an impression. Various exemplary embodiments of the present teachings may be used with an implant in which the implant shoulder that meets the abutment extends above the gingival tissue, is at the level of the tissue, or is slightly below the tissue, such as, for example, so-called "single-stage implants," although such use is not intended to be limiting. In various exemplary alternative embodiments, the present teachings may be used with an implant having an implant shoulder that is "submerged," or placed below the bone, and an abutment is provided with a shoulder portion that provides the finish line for the apical end of a mating component.

Moreover, it is contemplated that the various components may be used in conjunction with various implant configurations, such as conventional implant configurations that include but are not limited to, for example, various Solid Screw and Tapered Effect Implants made by ITI Straumann, including but not limited to the 4.1 mm and 4.8 mm Solid Screw and Tapered Effect Implants, and the 4.8 mm Wide Neck Solid Screw Implant and Tapered Effect Implant; Keystone Stage-1 and XP implants; BlueSkyBio One Stage Implant w/Regular and Wide Platform, Osstem SS Implant with Solid and Excellent Solid, 3I TG implant, and Zimmer's SwissPlus implant, among others. Implants with which various exemplary embodiments are configured to be used may also include a variety of coronal configurations for mating with abutments in accordance with the present teachings, including, but not limited to, for example, tapered internal coronal necks (e.g., conically-tapered internal coronal necks) and/or indexed (e.g., polygonal) anti-rotational internal coronal neck features, with which those having ordinary skill in the art are familiar. Those having ordinary skill in the art will appreciate a wide variety of conventional implants and other implant structures with which the various components in accordance with the present teachings may be utilized.

In various alternative exemplary embodiments, abutments in accordance with the present teachings may be formed integrally as a single-piece structure with the implant rather than being formed as a separate engageable component.

In accordance with various exemplary embodiments, the present teachings contemplate an abutment configured for engaging or made integral with a dental implant that includes one or more retention grooves on an outer peripheral surface (e.g., an outer lateral surface) thereof and configured to engage with one or more protrusion features on an impression coping for taking an impression of the abutment and implant fitted in a patient's mouth. In various exemplary embodiments, the impression copings may be made of metal, a metal alloy, and/or other radiopaque material capable of being observed in an X-ray. Abutments in accordance with various exemplary embodiments of the present teachings also may include one or more retention grooves on a outer peripheral surface thereof that are configured to engage with one or more protrusion features on a temporary coping or permanent restoration framework in order to achieve mechanical securing of a temporary or permanent restoration to the abutment, without requiring the use of cement or other bonding mechanism. The one or more retention grooves may have a radiused surface profile, meaning that the retention groove may be formed so as to present a radius of curvature.

In an exemplary embodiment, an abutment of the present teachings does not include a significant shoulder portion adjacent the one or more retention grooves in an apical direction. In other words, the widest portion of the abutment does not extend radially beyond a shoulder of the coronal neck of an implant with which the abutment is configured to mate. Thus, abutments in accordance with various exemplary embodiments of the present teachings may permit a mechanical securement of a component (e.g., impression and/or temporary coping, and/or permanent restoration framework) to the abutment while achieving a finish line of the component with an implant shoulder. In other words, when secured to an abutment in accordance with various exemplary embodiments of the present teachings, apical ends of various components of the present teachings may engage the implant shoulder rather than a portion, for example, a shoulder portion, of the abutment. In an alternative exemplary embodiment, however, an abutment of the present teachings may include a shoulder portion adjacent the one or more retention grooves in an apical direction and that is configured to provide the finish line surface with the apical ends of components supported by the abutment.

Providing the securing (retention) engagement of the components with the abutment, rather than, for example, with a portion of the implant, may facilitate placing the copings in an engaged manner in a patient's mouth. For example, since the portion of the abutment carrying the retention mechanism generally sits higher relative to the gumline (and in at least some cases is above the gumline) than the implant, engaging a component with the abutment in accordance with the present teachings may be easier because less or no gingival tissue may be needed to be pushed out of the way during expansion of the component to achieve the retaining engagement (which may be, for example, a snap-fit engagement) between the one or more protrusion features on the component with the one or more retention grooves on the abutment. Moreover, dampening of tactile and/or auditory sensation may be minimized during the engagement of the component with the abutment, thus promoting confirmation that the component has been accurately secured. The configurations of the components and abutments according to various exemplary embodiments of the present teachings also may require less or no bonding material (e.g., cement) when securing the copings to the abutment. For example, it may be possible to provide a sufficient retention of a temporary coping and/or framework by relying on the mechanical mating engagement (e.g., snap-fit engagement) between those structures and abutments in accordance with various exemplary embodiments, without requiring additional bonding material, such as cement or other adhesive.

Further, in cases where it may be desirable to use cement, it may be possible to use less cement because of the decrease in the overall size of a restoration resulting from an analog in accordance with exemplary embodiments having a size substantially the same as the abutment.

The present teachings additionally contemplate an analog used in a dental laboratory and having a configuration that is substantially identical in size to that of the abutment, also including one or more retention grooves that mimic those on the abutment and may be configured to engage with one or more protrusion features on burnout copings used to ultimately form a cast metal framework for a permanent restoration.

The drawings included herewith as part of the specification contain various dimensions, tolerances, and/or other specifications that are not intended to be limiting of the present teachings or the scope of the invention herein. Rather, the dimensions, tolerances, and/or other specifications noted on the drawings represent an exemplary embodiment of the various components depicted. Those having ordinary skill in the art would understand that modifications to such dimensions, tolerances and/or other specifications may be made as desired and in accordance with the present teachings without departing from the scope of the present teachings.

For ease of reference herein, a single framework used to form a permanent restoration to secure to an abutment and relative to a dental implant is described and shown herein. It is to be understood, however, that the present teachings contemplate that the term "framework" also includes a framework whereby a plurality (generally 2) single frameworks are connected together to form multiple restorations configured to be secured relative to multiple implants in a patient's mouth. Those having ordinary skill in the art are familiar with forming such multiple restoration framework structures and would understand how to modify the present teachings to apply to such frameworks.

As used herein, those having ordinary skill in the art are familiar with the meaning of the terms "apical" and "coronal." As used herein, "apical" refers to a direction toward the jaw bone, or toward root tips of teeth. If the term "apical" is used to refer to a portion of a component, it refers to the portion of the component that would be facing, closer to, and/or in a direction of the jaw bone and/or root tips if the component were placed in an operational position in a patient's mouth. The term "coronal" refers to a direction opposite the jaw bone and toward the crowns of teeth. If the term "coronal" is used to refer to a portion of a component, it may refer to the portion of the component that would be facing, closer to, and/or in direction of the crown portion of teeth if the component were placed in an operational position in a patient's mouth.

With reference now to FIG. 1, one exemplary embodiment of an abutment 100 for use with a dental implant is depicted. The abutment 100 includes an implant (or apical) end 180 that engages with the implant and a coronal end 190 that receives a restoration and/or other components configured to be secured to the abutment as will be set forth in more detail below. The abutment 100 may further include an implant engaging post 185 that includes the apical end 180 and comprises screw threading 110 configured to engage with complimentary screw threading on an internal surface of a dental implant.

Figure 18:
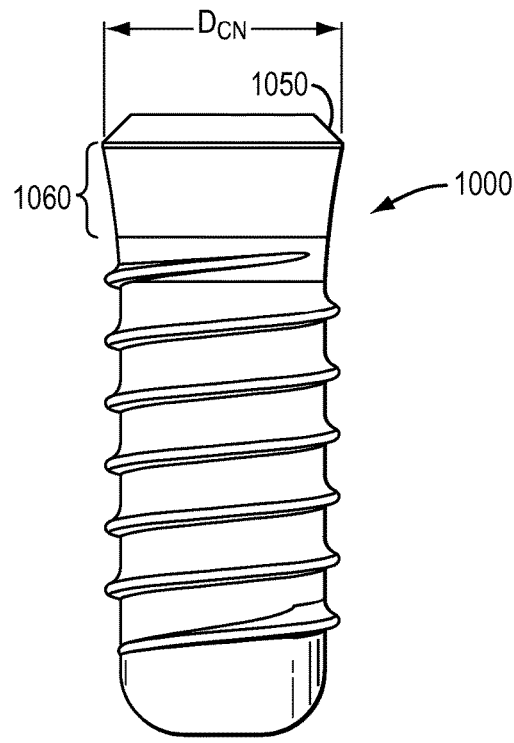
FIG. 18 is a side view of an exemplary embodiment of a dental implant in accordance with the present teachings.
Figure 20:
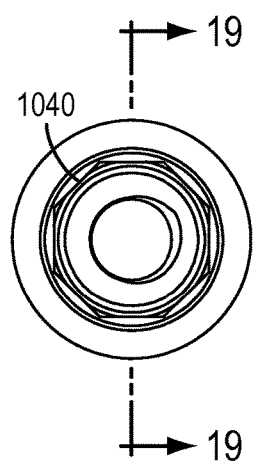
FIG. 20 is a coronal end view of the implant of FIG. 18.
Figure 19:
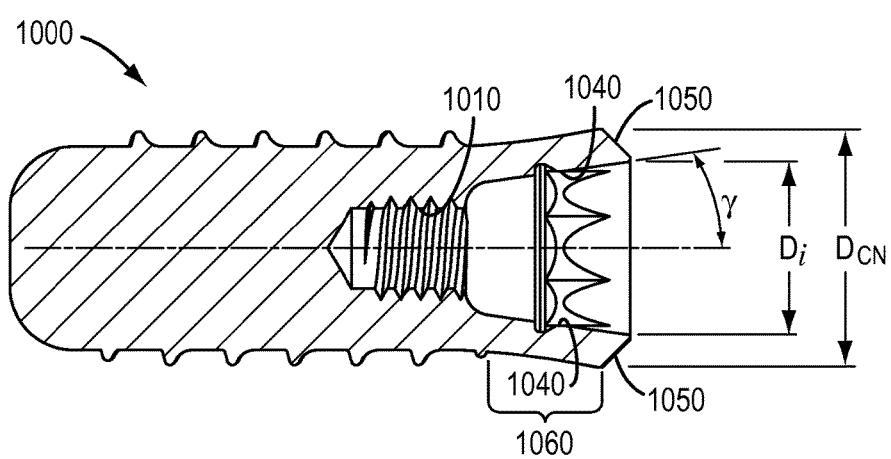
FIG. 19 is a cross-sectional view of the implant of FIG. 18 taken from the line 19-19 in FIG. 20.
Figure 21:
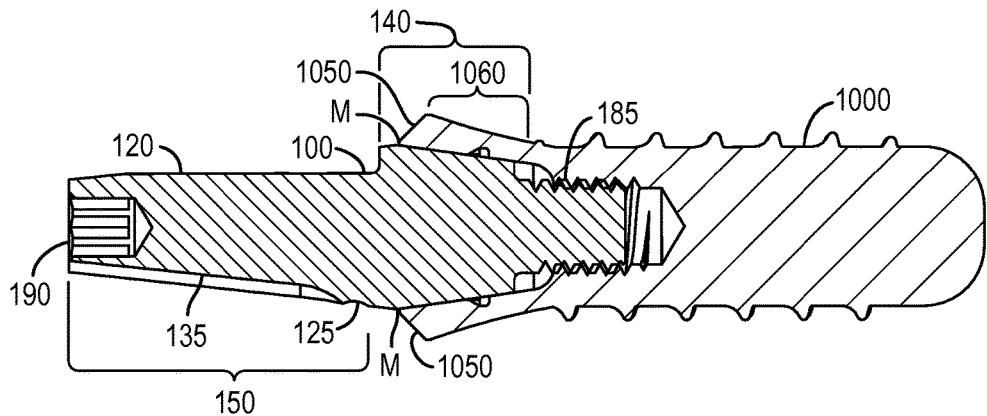
FIG. 21 is a longitudinal cross-sectional view of the abutment of FIGS. 1-5 in mating engagement with the implant of FIGS. 18-20.

One exemplary embodiment of an implant 1000 with which the abutment 100 may be configured to engage is shown in FIGS. 18-20. FIG. 21 shows a longitudinal cross-sectional view of the abutment 100 in a secured mating engagement with the implant 1000. As shown in the exemplary embodiment of FIG. 19, the implant 1000 may include internal screw threading 1010. The screw threading 1010 may be configured to engage with the screw threading 110 of the abutment 100. In the exemplary embodiment of FIGS. 18-20, the implant 1000 may be configured as a single-stage implant whereby a coronal neck 1060 is situated above the bone when implanted. The implant 1000 includes a shoulder portion 1050 located adjacent and coronal to the coronal neck 1060. A coronal neck diameter $D_{CN}$ is defined where the coronal neck 1060 meets the shoulder 1050. When abutments in accordance with various exemplary embodiments (e.g., the abutment 100) of the present teachings are secured in mating engagement to the implant 1000, the finish line (i.e., where an apical end of the component rests) of the components that are secured to the abutments may be located at the shoulder 1050 of the implant 1000.

Referring again to FIGS. 1-5, the coronal end 190 of the abutment 100 includes a recess 115, shown in more detail in FIGS. 3 and 4, that is configured to receive a screw driver or other tool used to drive the abutment 100 into the implant 1000, as will be explained in further detail below.

Although screw threading 110 is shown in the exemplary embodiment of the abutment 100, those having ordinary skill in the art would understand that various other engagement mechanisms may be utilized in lieu of or in addition to screw threading to engage the post 185 of the abutment with a dental implant. For example, rather than screw threading, a non-threaded implant engaging post may be utilized that is received in a corresponding opening in the implant, with the abutment being tapped into secure engagement with the implant. By way of example, such posts may provide an anti-rotational and secure engagement of the abutment with the implant, for example, by being tapered and configured to fit within a similarly tapered opening in the implant, by having a lateral surface that is polygonal in cross-section (e.g., hexagonal or octagonal) and configured to fit within a similarly configured opening in the implant, or a combination thereof. Those ordinarily skilled in the art would be familiar with various types of engagement mechanisms that could be used to secure the abutment to the implant, including, for example various internal or external polygonal and anti-rotational surfaces, tapered surfaces, lobed channels, and/or combinations thereof. Depending on the type of engagement mechanism, therefore, the opening 115 for receiving a screw driver or other tool may not be needed.

As illustrated in FIG. 2, the abutment 100 defines a substantially frustoconical portion 140 extending from the implant engaging post 185 to a location about mid-way to about ⅔ of the length L of the abutment 100 measured from the apical end 180. The frustoconical portion 140 of the abutment 100 has a peripheral outer surface that tapers at an angle α. The frustoconical portion 140 defines a shoulder 130 where the portion 140 meets the post 185.

The frustoconical portion 140 may be configured to engage with an internal frustoconical seat region on an implant, e.g., region 1040 in FIG. 19. In various exemplary embodiments, the angle, a, of the peripheral surface of the frustoconical portion 140 is configured to correspond to a tapered internal surface portion (i.e., seat region 1040 in FIG. 19) of the coronal neck of an implant that receives the abutment 100. Providing such a taper on the abutment, the angle of which may substantially correspond to the taper angle of an internal surface portion at the coronal neck of the implant with which the abutment mates (such as, for example, angle .gamma. shown in the exemplary implant of FIG. 19), may provide a substantially flush mating engagement between the abutment and the implant, which may enhance the accuracy of the fit and proper seating of the abutment on the implant. In various exemplary embodiments, the frustoconical portion 140 may be configured similar to a Morse taper (albeit at a different taper angle), which may render the abutment 100 non-rotational under occlusal (chewing) load once seated in the implant coronal neck portion; in other words, taking more force to unscrew the abutment to loosen it than to secure it to the implant. In lieu of or in addition to having the tapered frustoconical portion 140 that engages with the coronal neck of the implant, the portion 140 may present a polygonal (e.g., hexagonal or octagonal) peripheral surface that mates with a corresponding polygonal internal coronal neck surface of an implant.

In various exemplary embodiments, the angle $\alpha$ of the taper of peripheral surface of the frustoconical portion 140 may range from about 1.5° to about 15°, for example, about 5° to about 10°. For example, various implants with which the abutment 100 may be configured to engage may have an internal frustoconical coronal neck opening (e.g., seat region 1040) having an internal taper angle $\gamma$ ranging, for example, from about 1.5° to about 15°. For example, the taper angle may be about 1.5°, about 5.8°, about 8°, about 11° or about 15°, and thus, the angle $\alpha$ may be about 1.5°, about 5.8°, about 8°, about 11°, or about 15°, respectively. As is also depicted in the exemplary embodiment of FIG. 2, the abutment 100 includes a component supporting portion 150 extending from approximately mid-length to ⅔ the length L of the abutment 100 from the coronal end 190 to the apical end 180. The component supporting portion 150 may have a peripheral surface that tapers inwardly toward the end 190. As can be seen best in FIGS. 1 and 5, the portion 150 also may include a flat surface portion 120 configured to assist in preventing relative rotation of a restoration and/or other components and the abutment 100 during engagement therebetween. In various exemplary embodiments, the flat surface portion of the abutment may be disposed at a distance ranging from about 0.03 in. to about 0.065 in. from the centerline of the abutment, for example, the distance of the flat surface portion to the centerline of the abutment may be about 0.0492 in.

Figure 5:
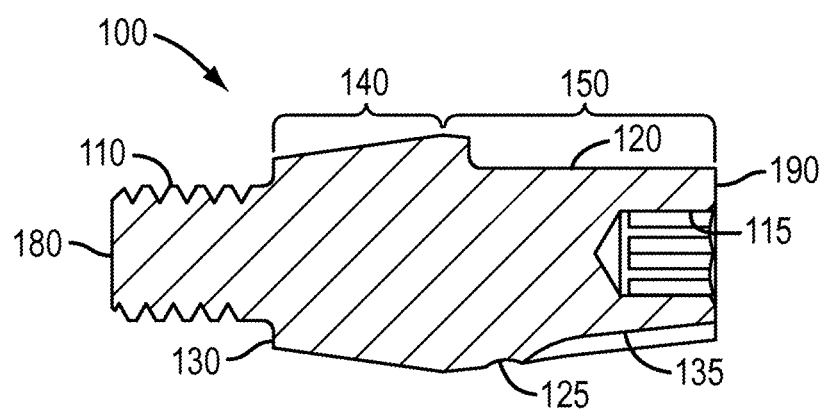
FIG. 5 is a cross-sectional view taken through line 5-5 in FIG. 3.

The exemplary embodiment of the abutment 100 also may include a longitudinal groove 135 on an external surface portion that is substantially opposite to the flat surface portion 120 and extends from the coronal end 190 in a direction along the length of the abutment, shown best in FIGS. 3-5. As is explained further below, the groove 135 extends in a direction substantially along the length of the abutment 100 and provides a gripping region for a tool used to torque the abutment 100 into engagement with an implant.

As mentioned above, in various exemplary embodiments, the portion 150 may taper at an angle, $\beta$ (see FIG. 2), ranging for example, from about 4° to about 8°, for example, from about 5.5° to about 6.5°, for example, the angle $\beta$ may be about 6°.

Around the outer peripheral surface of the component supporting portion 150 of the abutment 100 is a retention groove 125 that extends in a direction substantially transverse to a longitudinal axis of the abutment 100. More specifically, in the exemplary embodiment of the abutment 100 shown in FIGS. 1-5, the retention groove 125 may be positioned at or just coronal to the widest cross-sectional portion (at $D_a$ in FIG. 2) of the abutment 100 substantially where the frustoconical portion 140 and the component supporting portion 150 meet. The retention groove 125 may be configured to engage with one or more protrusion features on a component to achieve a mechanical retention (e.g., via a snap-fit engagement) of the component on the abutment. Such components may include but are not limited to, for example, an impression coping, a temporary coping, and/or a framework for a permanent restoration, exemplary embodiments of which will be described in further detail below. In various exemplary embodiments, one or more retention grooves, such as, for example, retention groove 125, may be positioned along a length of the portion 150 that is located just above an implant in the coronal direction when the abutment 100 is in engagement with the implant and fully inserted in the implant in an operational position. For example, in the exemplary embodiment of FIG. 2, the retention groove 125 may be positioned about midway to two-thirds along the length L of the abutment 100 from the implant end 180. In an exemplary embodiment, the one or more retention grooves may be positioned from about 0.025 in. to about 0.119 in. from the implant/abutment juncture (e.g., labeled as M in FIG. 21), which juncture may correspond approximately to where $D_a$ is in FIG. 2.

In various exemplary embodiments, the retention groove 125 may have a radiused surface profile. The surface of the retention groove 125 may, for example, define a radius of curvature ranging from about 0.010 in. to about 0.060 in. The retention groove 125 in the exemplary embodiment of FIGS. 1-5, extends about 270° around the outer peripheral surface of the abutment 100, for example, extending substantially around the entire periphery of the abutment 100 with the exception of the flat portion 120. In various exemplary embodiments, such a retention groove may have a height $h_g$ (measured along the longitudinal axis of the abutment 100) ranging from about 0.015 in. to about 0.040 in., for example, about 0.021 in. In an exemplary embodiment, the retention groove 125 may be machined to a depth ranging from about 0.001 in. to about 0.006 in., for example, 0.003 in.

As mentioned above, the flat surface portion 120 of the abutment may be about 0.03 in. to about 0.065 in. from the centerline of the abutment. That distance may vary and be selected, however, depending on the size, for example, the diameter of the component supporting portion 150, of the abutment. For example, the distance of the flat surface portion 120 to the centerline of the abutment 100 may be about 65% to about 80%, for example, about 72%, of the radius at the corresponding axial location on of the component support portion. By way of non-limiting example only, for an abutment configured to mate with an implant having a 4.1 mm (0.161 in.) coronal neck diameter (i.e., diameter $D_{CN}$ as illustrated in FIGS. 18 and 19), the flat surface portion 120 may be about 0.0366 in. from the centerline of the abutment. For an abutment configured to mate with an implant having a 4.8 mm (0.0189 in.) coronal neck diameter $D_{CN}$, the flat surface portion 120 may be about 0.065 in. from the centerline of the abutment. And for an abutment configured to mate with an implant having a 6.5 mm (0.256 in.) coronal neck diameter $D_{CN}$, the flat surface portion 120 may be about 0.060 in. from the centerline of the abutment.

Although the exemplary embodiment of FIGS. 1-5 depicts a single retention groove 125, those having ordinary skill in the art will appreciate that two or more retention grooves separated by non-grooved portions also may be provided around the outer peripheral surface of portion 150 of the abutment, but substantially at the same axial location along the length of the abutment, and disposed at locations so as to enable one or more protrusions on a coping (or other component) to engage in a snap-fit manner therewith. Moreover, retention grooves in accordance with various exemplary embodiments, rather than extending around all or a portion of the outer peripheral surface, could provide an indented relatively local radiused configuration configured to engage with one or more protrusion features on a coping or other component utilized with dental implant systems to provide a snap-fit engagement to the abutment.

In various exemplary embodiments, the one or more retention grooves provided on the outer peripheral surface of the abutment may be positioned so as to be accessible just above, at, or just below the gumline, when an abutment is positioned in place relative to an implant in a patient's mouth. Such positioning of the retention groove(s) may facilitate engagement of a corresponding protrusion on a coping or framework by, for example, making it easier to push the tissue out of the way during engagement and/or by making it easier to receive a sensation (such as, for example, tactile and/or auditory) confirming a snap-fit engagement between one or more protrusions and the retention groove. Placement closer to the tissue margin also may provide enhanced stability of the mounting of the component on the abutment by providing retention at a wider portion of the abutment that presents a larger retention surface area (e.g., the retention groove presents a relatively large surface are when placed close or at the widest portion of the abutment). Likewise, in cases where bonding, for example, by cement or other adhesive, of a component to the abutment may be desired, a greater surface area on the wider portion of the abutment may promote a more stable bonding. For abutments configured to be situated at or below the gumline, it may be desirable (although not necessary) to position the one or more retention grooves somewhat closer to the coronal end of the abutment than the groove 125 is disposed.

In accordance with various exemplary embodiments, the component supporting portion 150 may have a length ranging from about 4 mm (0.157 in.) to about 7 mm (0.276 in.), for example, about 4 mm, about 5.5 mm (0.216 in.) or about 7 mm. Likewise, abutments in accordance with various exemplary embodiments of the present teachings may have various diameters ($D_a$ in FIG. 2) where the abutment 100 mates with the implant substantially at a location of the shoulder of the implant (e.g., at location M shown in FIG. 21) so as to be configured to mate with implants having various coronal neck diameters, such as, for example, coronal neck diameters $D_{CN}$ of about 4.1 mm, about 4.8 mm, or about 6.5 mm. In various exemplary embodiments, the diameter $D_a$ may be about 2.7 mm (0.106 in.), 3.5 mm (0.138 in.), or 4.3 mm (0.169 in.), respectively, to engage with coronal neck diameters of about 4.1 mm, about 4.8 mm, or about 6.5 mm, respectively.

Those having ordinary skill in the art would understand, however, that the dimensions of abutments and corresponding portions thereof may be modified in accordance with the present teachings in order to fit with various implant configurations, coping configurations, framework configurations, and/or as desired to satisfy a particular patient and/or need; the dimensions set forth herein are non-limiting and exemplary only. For example, those ordinarily skilled in the art would appreciate a variety of abutment dimensions selected so as to mate with a variety of internal, conically-tapered implant configurations, with which those having ordinary skill in the art are readily familiar.

In an exemplary embodiment, the abutment 100 may be machined in order to provide precise tolerances of the various features of the abutment, including, for example, the one or more retention grooves, the tapered portions, etc., so as to ensure an accurate and precise fit with the implant and/or other components configured to be secured to the abutment. In an exemplary embodiment, the abutment may be made from cold-worked, commercially pure, Grade 4 titanium or other medical grade titanium or titanium alloy. However, any bio-compatible material providing sufficient strength and durability, such as, for example, a variety of biocompatible titanium materials, may be used to make an abutment in accordance with various exemplary embodiments of the present teachings. Although using a radiopaque material for the abutment may provide sufficient strength, for example to withstand occlusal loads, as well as permitting X-ray observation, other materials also may be suitable, including, for example, composites comprising ceramic and zirconium, composites comprising titanium and zirconium, and other zirconium composites or alloys.

As described above, abutments in accordance with various exemplary embodiments, such as the exemplary embodiment of FIGS. 1-5, may be configured to be screw-retained in the implant and thus may be configured to be torqued into the implant. By way of example, the abutment may be configured to be torqued in a range from about 25 Newton-centimeters (N-cm) to about 50 N-cm, for example, about 30 N-cm to about 35 N-cm. As mentioned above, the abutment 100 may be torqued via a screwdriver received in the recess 115, such as, for example by a standard 0.048 in. or 0.035 in. hex screwdriver, 4-lobe, or a standard torx.

The recess 115 and the groove 135 may be configured to form two mating configurations useful for permitting a screwdriver, torx or other tool to grip the abutment 100 to drive the abutment 100 into the implant with sufficient torque. The recess 115 may penetrate into the length of the abutment 100, for example, a distance ranging from about 0.030 in. to about 0.12 in. For example, for abutments configured to mate with implants of 4.1 mm or 4.8 mm coronal neck diameters ($D_{CN}$ in FIG. 19), the recess 115 may penetrate into the length of the abutment 100 a distance ranging from about 0.030 in. to about 0.075 in., and for abutments configured to mate with implants of 6.5 mm coronal neck diameter, the distance may range from about 0.065 in. to about 0.12 in. As shown in FIGS. 3 and 4, the recess 115 may have a substantially hexagonal perimeter configured to receive a hex screw driver.

In various exemplary embodiments, by placing one or more retention grooves on an abutment, as opposed to, for example, on an implant, permits a relatively wide range of torque to be used to secure the abutment to the implant without comprising the ability to achieve an accurate seating of the mating components relative to the abutment and the implant.

In various exemplary embodiments, the present teachings also contemplate angled abutments comprising one or more retention grooves configured to mate with one or more protrusion features (e.g. via snap-fit engagement) to achieve retention of various components (e.g., impression, temporary and/or frameworks) to be secured thereto. Those having ordinary skill in the art are familiar with angled abutments and one exemplary embodiment of a grooved angular abutment 3900 in accordance with the present teachings is depicted in FIG. 39. In FIG. 39, the abutment 3900 is shown secured in place relative to an implant 4000. The component supporting portion 3950 is disposed at an angle relative to a longitudinal axis of the implant 4000 (or from the vertical direction in the view of FIG. 39), which angle may, in various exemplary embodiments, range from about 15° to about 30°, for example, the component supporting portion 3950 may be at an angle of about 15° or, for example, about 20°. from vertical. As with other exemplary embodiments described herein, the abutment 3900 includes a retention groove 3925 on the portion 3950 proximate where the abutment 3900 meets the implant 4000. The dimensions and placement of the retention groove 3925 may be substantially the same as those described above with reference to other exemplary abutment embodiments. In the exemplary embodiment of FIG. 39, the abutment 3900 has a substantially frustoconical profile without a flat surface portion and the groove 3925 extends 360° around the periphery of the portion 3950. Those having ordinary skill in the art will appreciate that, as with other embodiments described above, the retention groove 3925 may extend less than 360° around the periphery and/or more than one groove 3925 may be provided substantially in the same axial plane and spaced from one another around the periphery. The abutment 3900 may also include an opening 3901 configured to receive a screw for screw-retaining the abutment to implant. Various other features of the angled abutment 3900 may be similar to those described above with reference to FIGS. 1-5.

Various exemplary embodiments of abutments in accordance with the present teachings also lend themselves to permitting custom platform sizing of restorations that are made and engaged thereto. That is, when creating a restoration, the outer diameter of the apical end of the restoration which meets the shoulder of the implant of the restoration when placed in snap-fit engagement with the abutment may be selected within a range of diameters that are smaller than the coronal neck diameter and up to and including the coronal neck diameter. By way of non-limiting example only, for a 4.1 mm coronal neck diameter implant and abutment configured to mate therewith, the component apical end outer diameter may range from about 3.2 mm (0.126 in.) to about 4.1 mm, for example, to about 4.1 mm. For a 4.8 mm implant and abutment configured to mate therewith, the component apical end outer diameter may range from about 4.1 mm to about 4.8 mm, and for a 6.5 mm implant and abutment configured to mate therewith, the component apical end outer diameter may range, for example, from about 5.4 mm (0.213 in.) to about 6.5 mm. This custom platform sizing ability provides flexibility when creating the restoration. Moreover, the ability to permit custom platform sizing may result in preservation of crestal bone.

The combination of providing the retention mechanism between the abutment and an implant component (e.g., a coping), while retaining the finish line of the apical end of the component with the implant shoulder promotes the ability to accomplish platform sizing, as described above. This is because modifications can be made to the apical end (e.g., a change in diameter when performing platform sizing) without affecting the retention mechanism of the component to the abutment. In conventional systems that utilize a retention mechanism between the implant shoulder and the component, such sizing may not be practical (or possible) because of the need to also alter the location of the retention mechanism on the shoulder and the component.

Figure 6:
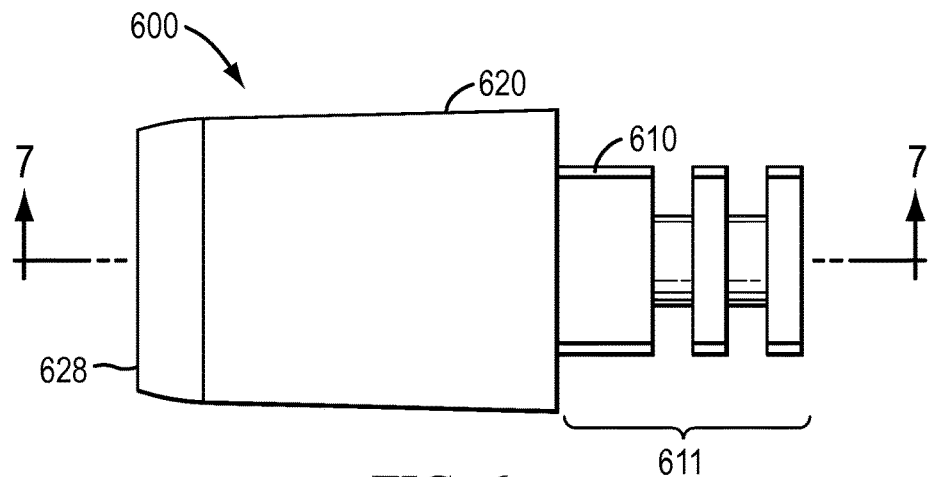
FIG. 6 is a side view of an exemplary embodiment of an impression coping in accordance with the present teachings.
Figure 7:
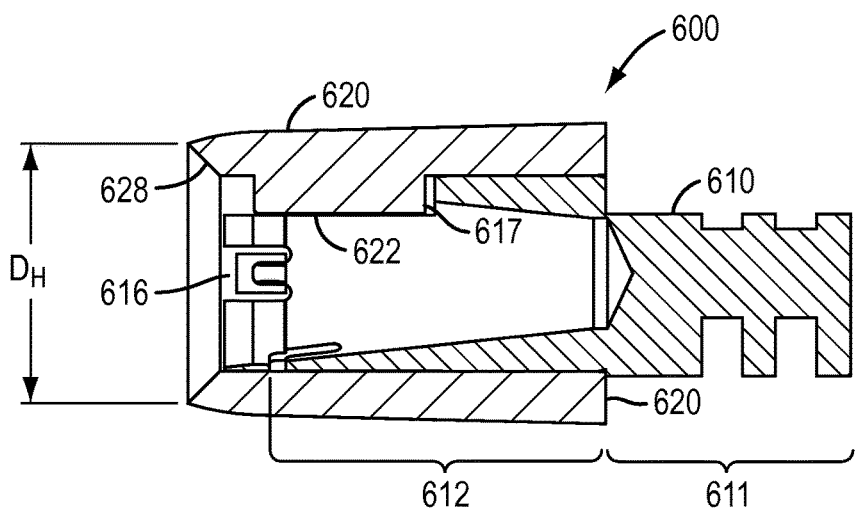
FIG. 7 is a cross-sectional view of the impression coping of FIG. 6 taken through line 7-7 in FIG. 6.
Figure 8:
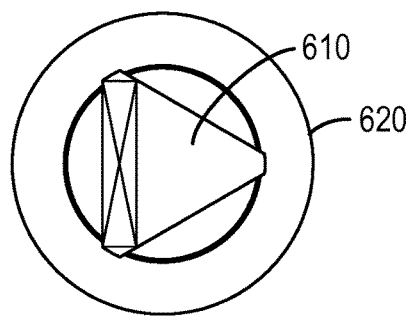
FIG. 8 is a coronal end view of the impression coping of FIG. 6.
Figure 9:
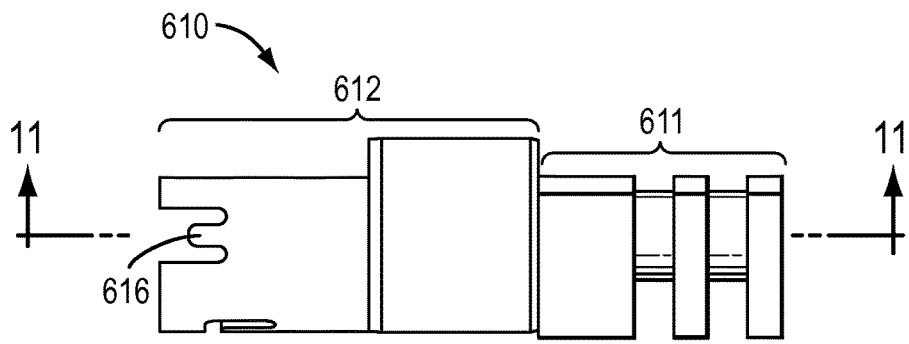
FIG. 9 is a side view of the insert of the impression coping of FIG. 6.
Figure 22A:
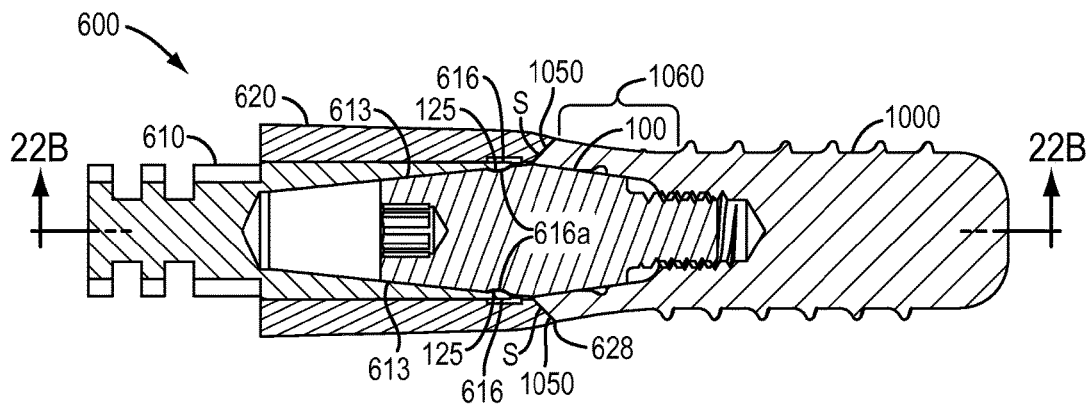
FIGS. 22A and 22B are longitudinal cross-sectional views in perpendicularly oriented planes of the impression coping of FIG. 6 engaged with the abutment and implant of FIG. 21.
Figure 22B:
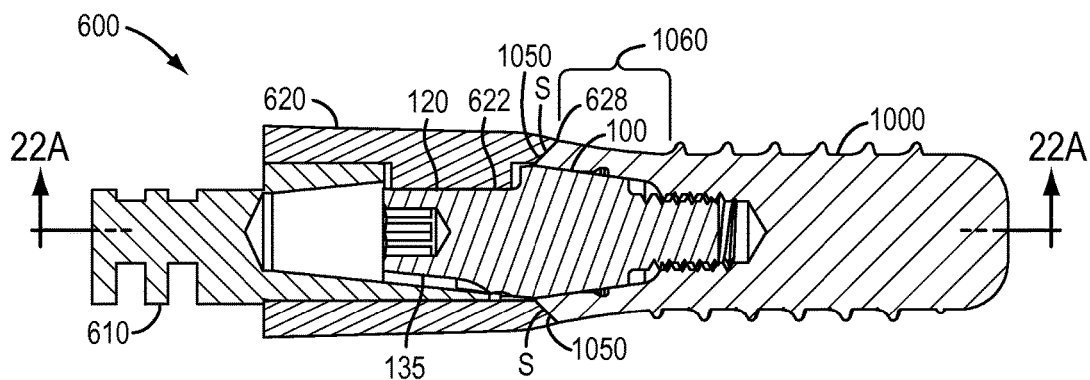
Figure 23:
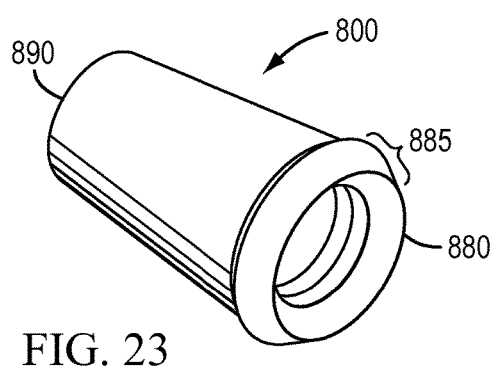
FIG. 23 is a perspective view of an exemplary embodiment of a temporary coping in accordance with the present teachings.

Referring now to FIGS. 6-17, and FIGS. 22A-22B, an exemplary embodiment of an impression coping, and parts thereof, that may be used with an abutment in accordance with various exemplary embodiments of the present teachings is illustrated. FIG. 6 illustrates a side view of an exemplary embodiment of an impression coping 600. FIG. 7 is a cross-section of the impression coping 600 taken through line 7-7 in FIG. 6, and FIG. 8 is an end view taken from the coronal end of the impression coping 600 in FIG. 6. As shown best in FIG. 7, the impression coping 600 may be a two-piece device comprising an insert 610 and a housing 620 configured for engagement with one another so as to form an integral structure. FIGS. 9-13 show various views of the insert 610, and FIGS. 14-17 show various views of the housing 620. FIGS. 22A and 22B show longitudinal cross-sectional views (taken in respective planes perpendicular to each other) of the impression coping 600 engaged with the abutment 100 and implant 1000.

The two-piece construction of the impression coping 600 may be desirable in order to permit the impression coping 600 (i.e., the insert 610 and housing 620) to be made from materials comprising metal. In this way, the impression coping 600 may be machined, as opposed to molded (e.g., via injection molding), to produce relatively high tolerances (compared to that than can be achieved via injection molding which can have tolerances up to about 10 times worse than machining) of various features of the impression coping, including but not limited to, for example, protrusion features and/or other internal features configured to produce a precise mating and accurate fit with an abutment, such as, for example abutment 100. In various exemplary embodiments, therefore, the present teachings contemplate an impression coping made from a material comprising metal, e.g., a metal, metal alloy, and/or composition comprising plastic and metal. Providing an impression coping made from such materials also makes the impression coping radioopaque and able to be viewed on an X-ray, which may facilitate the ability to achieve an accurate identification of the location and situation of an implant in a patient's mouth.

With reference to FIGS. 6-13, the insert 610 is configured to be received in the housing 620, with an impression portion 611 of the insert 610 extending from the housing 620 and an abutment engaging portion 612 of the insert 610 being received within the housing 610. The impression portion 611 is configured to be inserted into impression material when the impression coping 600 is placed in engagement with an abutment, for example, abutment 100, in a patient's mouth. The impression portion 611 may have a substantially serrated surface profile so that the impression coping 600 may be sufficiently grasped by impression compound, for example, in an impression tray, to facilitate removal of the impression coping 600 with the removal of the tray from the patient's mouth. In other words, the coping 600 may be configured as a so-called "pick-up coping," with which those having ordinary skill in the art are familiar. That is, the impression coping 600 may be configured to provide a relatively stable engagement with the abutment 100 with little or no movement when the impression is being taken, while also being able to be relatively easily disengaged from the abutment upon sufficient force being applied by lifting the impression coping 600 in a substantially vertical direction off of the abutment after impression material has been formed around the impression coping 600 and the impression of the abutment and implant location in a patient's mouth has been taken.

In an alternative exemplary embodiment, illustrated in FIG. 40, the impression portion of the impression coping may be provided on the housing, rather than on the insert. Thus, in the exemplary embodiment of FIG. 40, the housing 4620 of the impression coping 4600 includes a serrated outer surface profile indicated at 4611. The impression surface profile may be machined as part of the housing 4620, for example. Providing the impression portion 4611 as part of the housing 4620 in the exemplary embodiment of FIG. 40 may permit a reduction in the overall length of the impression coping 4600, thereby facilitating the ability to perform a bitewing registration on a patient with the impression coping 4600 in the patient's mouth. Other parts of the impression coping of FIG. 40 may be the same as the impression coping 600 and therefore are not described or labeled.

Figure 11:
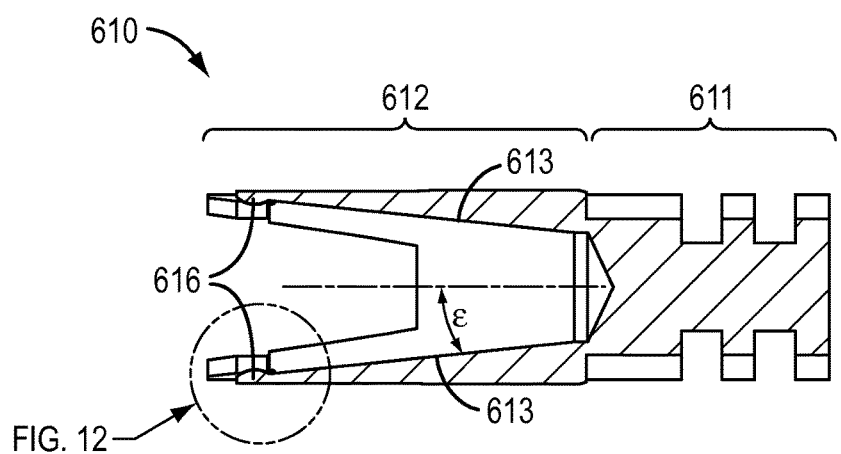
FIG. 11 is a cross-sectional view of the insert taken through line 11-11 of FIG. 9.
Figure 12:
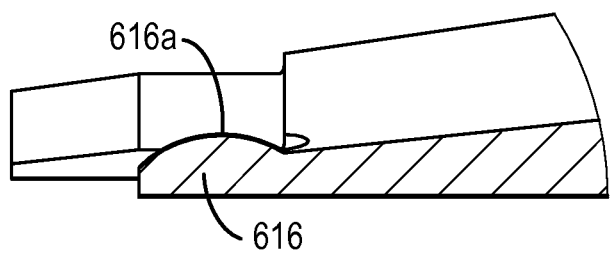
FIG. 12 is a detailed view of the portion labeled FIG. 12 in FIG. 11.

In various exemplary embodiments, the abutment mating portion 612 of the insert 610 may have internal surfaces (e.g., internal surface 613 shown best in FIGS. 11 and 22A) that are dimensioned and tapered so as to substantially correspond to the dimensions and taper of the component supporting portion of an abutment to permit the abutment to be received within in a flush mating engagement with the impression coping 600 (see FIGS. 22A and 22B). For example, the taper of the internal surface 613 may substantially correspond to the taper of the portion 150 of the abutment 100. By way of non-limiting example, the inner surface portion 613 of the insert 610 may taper toward the impression end of the coping 600 at an angle, c, as shown in FIG. 11. For example, the taper may be at an angle, c, ranging from about 4° to about 8°, for example, about 5.5° to about 6.5°, for example, about 6°.

Figure 10:
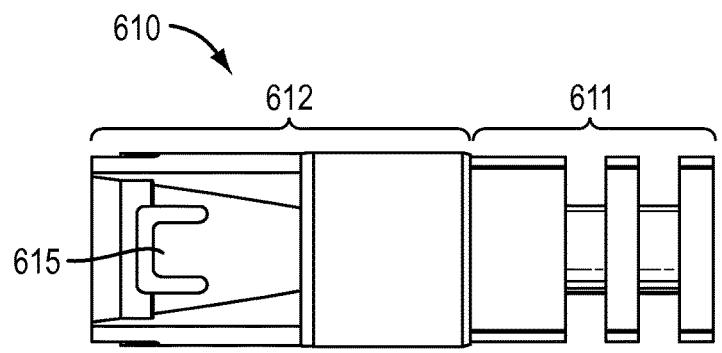
FIG. 10 is another side view of the insert of the impression coping of FIG. 6.
Figure 13:
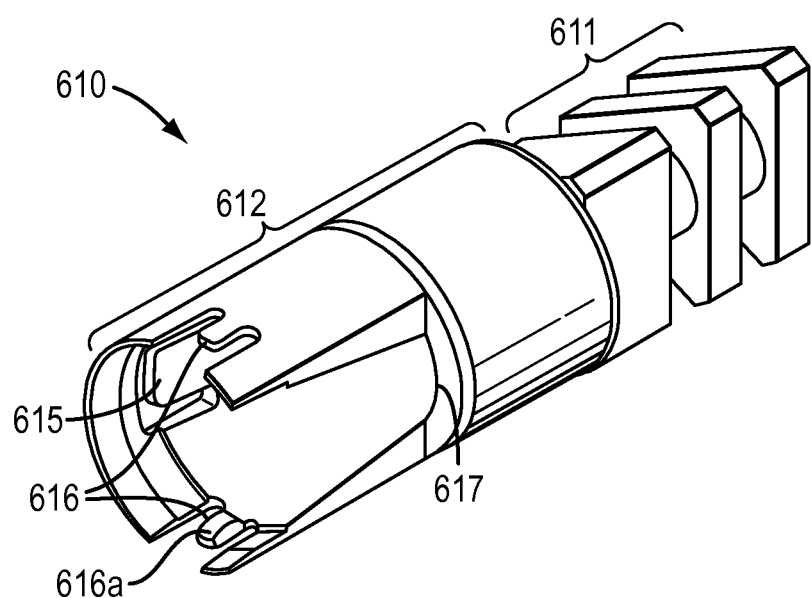
FIG. 13 is a perspective view of the insert of the impression coping of FIG. 6.
Figure 14:
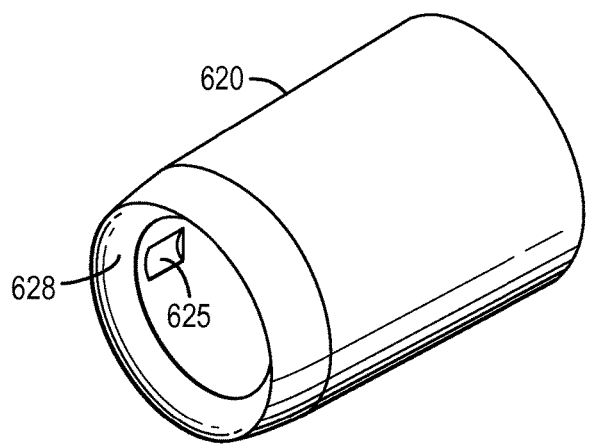
FIG. 14 is a perspective view of the housing of the impression coping of FIG. 6.
Figure 17:
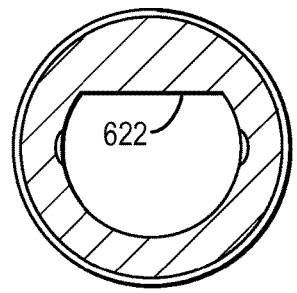
FIG. 17 is a cross-sectional view taken through line 17-17 of FIG. 15.
Figure 15:
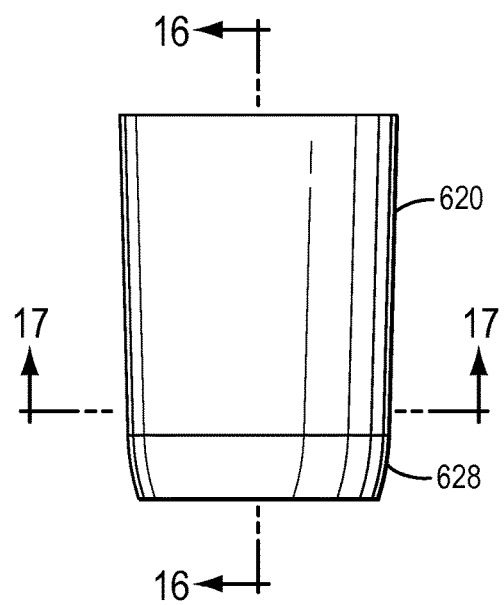
FIG. 15 is a side view of the housing of FIG. 14.
Figure 16:
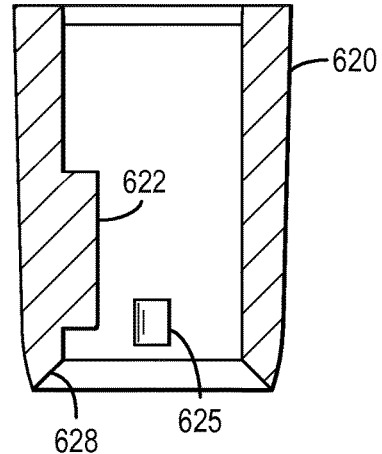
FIG. 16 is a cross-sectional view taken through line 16-16 of FIG. 15.

As best seen in FIGS. 7, 10, and 13, on a lateral surface of the insert 610 proximate an end of the insert 610 opposite the impression portion 611, at least one retaining feature 615 may be disposed. The retaining feature 615 may be disposed substantially opposite an opening 617 provided on the insert 610 that is configured to receive a protruding internal surface portion (622 in FIGS. 7, 16, and 17), which surface portion is configured to rest flush against a flat surface portion (e.g., flat surface portion 122) on a component supporting portion of an abutment in order to help accurate positioning of the coping relative to the abutment, as well as preventing or hindering rotation of the impression coping relative to the abutment. The at least one retaining feature 615 may be configured to engage with a corresponding opening 625 (shown in FIGS. 14 and 16) on an inner surface of the housing 620. In various exemplary embodiments, for example, as shown in FIGS. 7 and 10, the retaining feature 615 may be formed by a substantially U-shaped cut-out of the lateral wall of portion 612 proximate an apical end of the insert 610. The retaining feature 615 may be configured to be received in the opening 625, which may be formed in an interior surface of the housing 610 without penetrating through the thickness of the housing wall. When the retaining feature 615 is received in the opening 625, the insert 610 and housing 620 are in a mating engagement in which they are substantially prevented from rotating and or moving axially relative to each other.

The retaining feature 615 may be configured to be elastically deflectable in a radial direction (e.g., toward and away from a longitudinal axis of the insert 610) and may be slightly biased in a direction toward the longitudinal axis of the insert 610. In this way, while not wishing to be bound by any particular theory, it is believed that the retaining feature 615 may resiliently press against the abutment when the impression coping 600 is secured thereto to push the flat surface portion of the abutment (e.g., flat surface portion 122) against the surface portion 622 of the housing 620, which may thereby assist in preventing rotation of the impression coping 600 relative to the abutment when taking an impression. In various alternative exemplary embodiments (not shown), the impression coping insert 610 may be provided without the retaining feature 615 and the housing 620 without the corresponding opening 625. In such a configuration, the insert 610 and the housing 620 may be held together by an interference fit between those parts.

Referring now to FIGS. 9-12, the insert 610 may also include one or more deflection tabs 616 (two such tabs 616 being depicted in the exemplary embodiment of FIGS. 9-12), which may be formed by cut-outs, e.g., machined cut-outs, configured substantially as U-shaped slots at a free end of abutment engaging portion 612. The deflection tabs 616 may include localized protrusions 616a, which may be substantially semi-spherical in an exemplary embodiment, on an internal surface portion that are configured to mate with one or more retention grooves on an abutment in accordance with exemplary embodiments of the present teachings, for example, with the groove 125 on the abutment 100, as depicted in FIG. 22A. In this way, the impression coping 600 can engage and be retained by the abutment 100 via a secure mating engagement (which may be, for example, a snap-fit engagement) of the protrusions 616a with the retention groove 125. In this way, an accurate and secure fit between the impression coping 600 and the abutment 100 may be achieved. The engagement of the one or more protrusions 616a with the retention groove 125 may also provide a tactile and/or auditory sensation resulting from a snap-fit securement, thereby providing assurance to a user that accurate engagement has occurred. The ability of the tabs 616 to elastically deflect, and in particular when those tabs are made of a material comprising metal, may enhance the tactile and/or auditory sensation due to the tabs 616 "springing" back into position once they are advanced over the relatively wide region of portion 150 of the abutment 100 just above the retention groove 125 and then reach the retention groove 125.

In various exemplary embodiments, the engagement of the protrusions 616a with the retention groove 125 may be such that the impression coping 600 may be relatively easily disengaged and removed from the abutment during "pick up" (e.g., upon application of a sufficient vertical force lifting the impression coping off of the abutment) in the impression compound upon removal of the impression tray from the patient's mouth. The configuration of the tabs 616, with the U-shaped opening surrounding each tab 616, may permit some substantially elastic radial deflection of the tabs 616 to facilitate engagement of the protrusions 616a and retention grooves on an abutment for achieving the retention of the coping 600 on the abutment.

In the exemplary embodiment of the impression coping 600, the tabs 616 with protrusions 616a are disposed substantially opposite each other and about 90° apart from the retaining feature 615. Those ordinarily skilled in the art will appreciate however that any number of tabs 616 carrying protrusions 616a ranging from one to more than one may be provided and disposed as desired around the insert 610 so as to provide a mating engagement (e.g., a snap-fit engagement) with one or more corresponding retention grooves provided on an abutment to achieve retention of the impression coping with the abutment in accordance with the present teachings. Those having ordinary skill in the art would understand how to select the number and positioning of such tabs carrying protrusions based on various factors, including but not limited to, for example, the desired strength of engagement between the impression coping and the abutment, the desired ease of pick up of the impression coping, the number and/or position of mating retention grooves provided on the abutment, etc. In one exemplary embodiment, the force required to engage the one or more protrusion features on an impression coping with one or more retention grooves on an abutment (e.g., snap the impression coping on the abutment) may range from about 0.5 lb. to about 5 lb., and the force required to lift off the impression coping from an abutment may range from about 0.5 lb. to about 6 lb.

In various exemplary embodiments, the protrusions 616a have a convex surface profile facing an interior of the insert 610. In an exemplary embodiment, the radius of curvature of each protrusion 616a may be selected so as to form a mating engagement with a retention groove (e.g., retention groove 125) on an abutment. In an exemplary embodiment, the protrusions 616a may have a radius of curvature ranging from about 0.015 in. to about 0.025 in., for example, about 0.02 in., and may protrude from the internal peripheral surface portion of the tabs 616 from about 0.002 in. to about 0.006 in., for example, about 0.004 in. The height of the protrusions 616a measured in a direction along a longitudinal axis of the impression coping may be substantially the same as the height of a corresponding retention groove (e.g., height $h_g$) with which the protrusions are configured to mate. In various exemplary embodiments, the height of the protrusions 616a may range from about 0.015 in. to about 0.040 in., for example, about 0.021 in. In various exemplary embodiments, the protrusions 616a on the deflection tabs 616 may be configured to provide an interference grip with a retention groove on an abutment (e.g., retention groove 125) ranging from about 0.0005 in. to about 0.003 in., for example, about 0.001 in.

The above dimensions are, however, non-limiting and exemplary only; those having ordinary skill in the art would understand how to select other dimensions in order to provide desired results, which may include, for example, achieving a sufficient tactile and/or auditory sensation upon engagement of the protrusions on the impression coping with the one or more retention grooves on the abutment, achieving a secure mating engagement between the protrusion features on the impression coping with one or more retention grooves on the abutment so as to minimize movement of the impression coping during the taking of the impression, while still permitting the coping to be relatively easily "picked up" (e.g., removed from the abutment) with the impression compound tray after the impression is taken, and/or a variety of other factors that may influence the choice of dimensions. The choice of dimensions of the protrusions also may depend on the dimensions of the one or more retention grooves with which the protrusions will engage.

Although in the exemplary embodiment of FIGS. 6-17 and 22A-22B the protrusions 616a that engage with the retention groove(s) on the abutment are provided on the insert 610 of the coping 600, those having skill in the art would understand that protrusions could instead be provided on an inner surface portion of the housing 620 without departing from the scope of the present teachings.

Referring to FIGS. 7, 14, 16, and 17, the housing 620 may be configured as a substantially hollow cylinder having a beveled apical end region 628, the outer surface of which tapers inwardly toward the free apical end of the housing 620. As mentioned above, the housing 620 may include an inner lateral surface portion 622 that extends inwardly further than remaining inner surface portions of the housing 620 and that presents a substantially flat, as opposed to arcuate, surface. This inner surface portion 622 is configured to abut the flat surface portion of an abutment with which the coping 600 engages, such as, for example, flat surface portion 120 on the abutment 100. Alignment of the coping 600 relative to the abutment 100 and the prevention of relative rotation of the coping 600 and the abutment 100 may be achieved through the use of the inner surface portion 622 on the housing 620 and the flat surface portion 120 on the abutment 100 (the mating contact of which is shown in FIG. 22B). As mentioned above, and as shown best in FIGS. 7 and 13, the inner surface portion 622 may be received in the opening 617 when the insert 610 and the housing 620 are engaged with each other.

As mentioned above, an apical end region 628 of the housing 620 that is advanced over an abutment first during engagement of the impression coping 600 with an abutment may be beveled (e.g., angled or tapered toward the free end) so as to provide a surface that assists in pushing tissue away from the impression coping 600, if needed, during engagement of the impression coping with the abutment. As can be seen in the exemplary embodiment of FIGS. 22A and 22B, when the impression coping 600 is engaged with the abutment 100, the apical end region 628 provides a surface defining an apical opening of the housing 620 and that provides a flush mating engagement with the shoulder 1050 of the implant 1000 (the flush mating engagement identified by reference S in FIGS. 22A and 22B). Thus, in the exemplary embodiment of FIGS. 22A-22B, although the impression coping 600 is secured relative to the implant 1000 by a mating secure engagement with the abutment 100 (i.e., the mating engagement between the protrusions 616a and the retention groove 125), the impression coping 100 nonetheless provides a finish line (where the apical end of the impression coping rests) on the implant shoulder 1050 as opposed to a shoulder on the abutment, for example. In other exemplary embodiments, as will be explained in more detail below, the finish line between temporary copings and frameworks also may be at the implant shoulder 1050, rather than on the abutment 100. However, as will be described below, other exemplary embodiments of the present teachings contemplate an abutment provided with a shoulder that is configured to provide a finish line surface with various components (e.g., impression copings, temporary copings, and/or frameworks in accordance with exemplary embodiments) supported thereon and retained via the mating engagement (e.g., snap-fit engagement) between one or more retention grooves on the abutment and one or more protrusion features on such components. Thus, for example, the apical end 628 of the impression coping 600 may rest flush against a surface of a shoulder on an abutment, such as, for example, shoulder 4105 of the exemplary abutment 4100 in FIG. 41.

Providing the finish line at the implant shoulder, for example rather than on a part of the abutment such as an abutment shoulder, however, in accordance with various exemplary embodiments, may permit a shorter crown (restoration)/root ratio, which may decrease the risk of fracturing the implant or abutment. Moreover, under occlusal load, less force may be transferred to the engagement between the abutment and the implant which engagement can pose a source of failure if too large a load is applied thereto. Providing the finish line of a restoration on the shoulder of the implant rather than the abutment also can lead to a greater transfer of force to the implant body. By way of example, from about 85% to about 95%, for example, about 91% of the force, may be transferred to the implant during occlusal load, which load percentage may depend, for example, on the configuration (e.g., size) of the implant.

In various exemplary embodiments, impression copings in accordance with the present teachings may be made of a biocompatible metal, such as, for example, stainless steel, a titanium alloy, or other suitable biocompatible metal, or a composition comprising a biocompatible plastic and a biocompatible metal. Making the impression coping from radioopaque materials, such as, for example, materials comprising metal, may assist in viewing the impression coping on X-rays, which will help to achieve accuracy obtaining the location of the implant and/or in the constructing of a restoration. Alternatively, however, impression copings in accordance with various exemplary embodiments of the present teachings may be made of plastic materials. In the case of plastic materials, rather than the two-part configuration of the coping shown in the exemplary embodiment of FIGS. 6-17, the impression coping may be a single-piece construction formed, for example, via injection molding.

The dimensions of the impression coping can vary and may be selected based on, for example, the implant diameter at the coronal neck, examples of which are provided above, so as to provide a flush mating fit between the impression coping and the abutment as well as with the implant shoulder. By way of non-limiting example, the diameter $D_H$ (see FIG. 7) may range from about 2.6 mm (0.102 in.) to about 7 mm (0.276 in.), for example, about 4.1 mm, about 4.8 mm or about 6.5 mm. Also by way of non-limiting example, the length of the impression coping 600 from end to end may range from about 5 mm (0.197 in.) to about 12 mm (0.472 in.), for example, about 11 mm (0.433 in.). The length of the housing 620 from end to end may range from about 4 mm (0.157 in.) to about 8 mm (0.315 in.), for example, about 7 mm (0.276 in.).

Various exemplary embodiments in accordance with the present teachings thus contemplate the use of an impression coping, such as, for example, the impression coping shown and described with reference to the exemplary embodiment of FIGS. 7-17, that is retained in a secure and accurate manner on an abutment, such as abutment 100, to take an impression of the location and positioning of an implant in a patient's mouth. In alternative exemplary embodiments, however, the present teachings contemplate that abutments having one or more retention grooves may be used to take a direct impression of the patient's mouth, in particular, when the one or more retention grooves are exposed above the patient's gumline when the abutment is secured to the implant. In other words, impression material (e.g., light-body impression material) may be formed directly around the abutment secured to an implant in the patient's mouth, without using an impression coping. The one or more retention grooves may be formed deep enough so as to allow an analog to be retro-fitted into the impression mold from the direct impression to substantially prevent vertical movement relative to the analog while a stone model is being poured. Moreover, a flat surface portion of the abutment, such as, for example, flat surface portion 120, may register in the impression material the positioning of the abutment within the patient's mouth and may eliminate rotational movement in impression while the model is poured in the dental laboratory.

Figure 24:
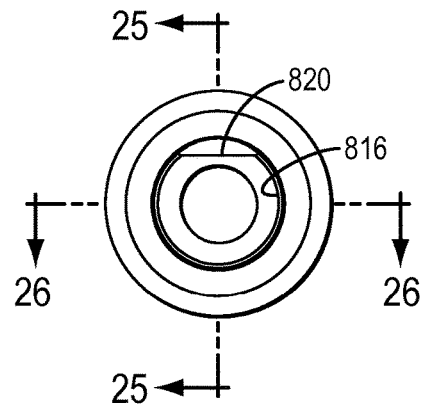
FIG. 24 is an apical end view of the temporary coping of FIG. 23.
Figure 25:
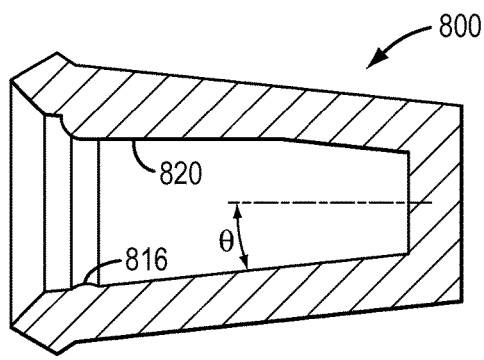
FIG. 25 is a cross-sectional view taken of the temporary coping of FIG. 23 taken through line 25-25 of FIG. 24.

Referring now to FIGS. 23-27, various exemplary embodiments of temporary copings in accordance with the present teachings are illustrated. In FIGS. 23-26, the temporary coping 800 has a tapered, substantially frustoconical, hollow configuration having an open apical end 880 and a closed coronal end 890. The temporary coping 800 is configured to be advanced over an abutment, such as abutment 100. As seen best in FIGS. 24-26 (FIG. 24 being an apical end view of FIG. 23; FIG. 25 being a cross-sectional view taken through line 25-25 in FIG. 24; and FIG. 26 being a cross-sectional view taken through line 26-26 in FIG. 24), provided on the internal peripheral surface of the temporary coping 800 proximate the apical end 880 is a protrusion feature in the form of a continuous protrusion ring 816 that extends, in the exemplary embodiment of FIGS. 23-26, around the inner peripheral surface of the coping 800 up to the flat surface portion 820. Similar to protrusions 616 on the impression coping 600, the protrusion ring 816 may be configured to provide a mating engagement with one or more retention grooves provided on an abutment, such as, for example, the retention groove 125 on the abutment 100. The protrusion ring 816 may have a convex profile and be configured to engage (e.g., in a snap-fit manner) with a retention groove, e.g, retention groove 125, on an abutment so as to form an accurate and secure retention of the temporary coping 800 on the abutment. In other words, the protrusion ring 825 may be configured to mate in a precise and flush manner with the retention groove 125 when the temporary coping 800 is advanced down over and into mating engagement (e.g., snap-fit) with the abutment 100.

As best shown in the FIGS. 24 and 25, an internal flat surface portion 820 of the temporary coping 800 may extend inwardly relative to the remaining surface portions. The flat surface portion 820 may present a substantially flat surface facing toward a center of the temporary coping 800, and may be configured to correspond and abut in a substantially flush manner with a flat surface portion on the abutment, for example, flat surface portion 120 on abutment 100, to prevent relative rotation of the temporary coping 800 relative to the abutment and/or to assist in alignment of the temporary coping 800 relative to the abutment.

Figure 26:
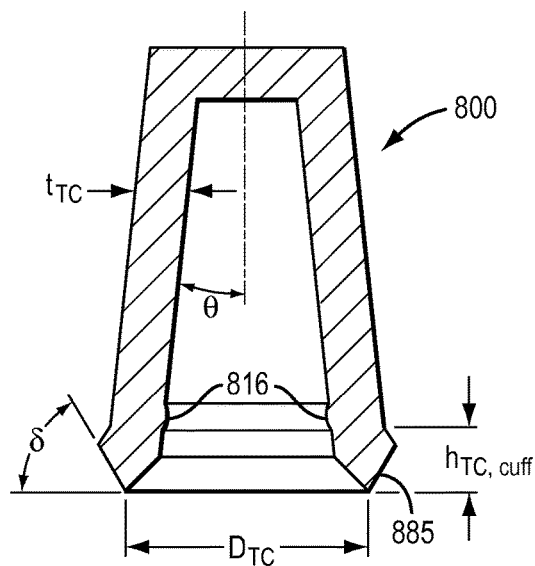
FIG. 26 is a cross-sectional view of the temporary coping of FIG. 23 taken through line 26-26 of FIG. 24.

As is perhaps best shown in FIGS. 25 and 26, the interior of the temporary coping 800 may present a tapered surface from the apical open end 880 toward the coronal end 890. The degree of taper may substantially correspond to the taper of the supporting portion of an abutment with which the temporary coping is engaged, such as, for example, portion 150 of abutment 100. For example, the angle of taper, θ, may range from about 4° to about 8°, for example, from about 5.5° to about 6.5°, for example, θ may be about 6°.

The length and other dimensions of the temporary coping 800 may be selected as desired based on the implant and abutment dimensions. By way of non-limiting example, temporary copings may be configured to fit with abutments that are configured to fit with implants having between 2.6 mm to 7 mm, for example, 4.1 mm, 4.8 mm or 6.5 mm coronal neck diameters. For example, the diameter $D_{TC}$ (see FIG. 26) may be sized so as to correspond to the coronal neck diameter of an implant with which the temporary coping is configured to engage. Thus, in various exemplary embodiments, $D_{TC}$ may range from about 2.6 mm to about 7 mm. For example, $D_{TC}$ may be about 4.1 mm, about 4.8 mm or about 6.5 mm. Alternatively, if platform sizing is desired, than $D_{TC}$ may be provided within a range, as explained above with reference to the description of platform sizing. In various exemplary embodiments, internal dimensions (such as, for example, the diameter and length) of the temporary coping 800 may be selected so as to provide a substantially flush mating surface contact (i.e., within machining tolerances) between the internal peripheral surfaces of the temporary coping 800 and the outer peripheral surfaces of the component supporting portion of an abutment (e.g., portion 150 of abutment 100) with which the temporary coping 800 is engaged.

The temporary coping may include a cuff 885 at the apical end 880 that permits patient-specific contouring of the temporary restoration to occur based on the gingival tissue height of the patient, as those having ordinary skill in the art are familiar with. The cuff 885 may have an angled outer surface, which may be disposed, for example, at an angle δ ranging from about 45° to about 75°, for example about 60°, from horizontal in the orientation of FIG. 26. The height of the cuff $h_{TC, cuff}$ (see FIG. 26) may range from about 1 mm (0.039 in.) to about 4 mm (0.157 in.), and the overall length (including the cuff 885) from the apical end 880 to the coronal end 890 may range from about 4 mm to about 9 mm (0.354 in.). In various exemplary embodiments, the thickness $t_{TC}$ of the walls of the temporary coping 800, except at the location of the flat surface portion 820, may range from about 0.02 in. to about 0.04 in.

The angled surfaces of end 880 of temporary coping 800, e.g., on the cuff 885, may facilitate moving tissue out of the way during engagement of the temporary coping 800 with the abutment. Moreover, similar to the impression coping described above with reference to FIGS. 6-16 and 22, the internal beveled surfaces of the end 880 may be configured to abut in a flush mating manner a shoulder of an implant, e.g., shoulder 1050, (or, a shoulder on an abutment (if any), e.g., shoulder 4105 in FIG. 41) when the temporary coping 800 is engaged with an abutment secured to an implant.

Figure 27:
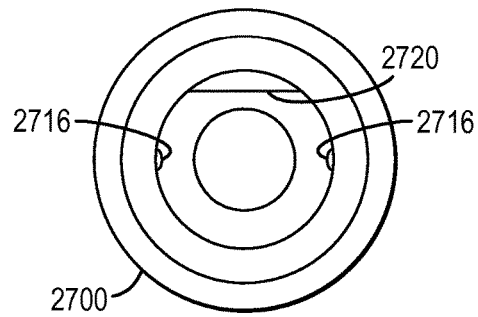
FIG. 27 is a cross-sectional view, similar to the view of FIG. 24, of another exemplary embodiment of a temporary coping in accordance with the present teachings.

Although the exemplary embodiment of FIGS. 23-26 show a temporary coping provided with a single continuous protrusion ring extending approximately 270° around an inner peripheral surface of the temporary coping, in an alternate exemplary embodiment, as depicted in the apical end view of FIG. 27, a temporary coping 2700 may be provided with one or more relatively localized protrusions 2716 configured to engage, e.g., in a snap-fit manner, with one or more retention grooves on an abutment in accordance with the present teachings. The temporary coping 2700 may include two protrusions 2716 disposed substantially opposite one another with the internal surface portion 2720 being disposed substantially midway between the two protrusions 2716. Other portions of the temporary coping 2700 may be substantially the same as those described above with reference to temporary coping 800. In yet another alternative exemplary embodiment (not shown), rather than a single protrusion ring, a temporary coping in accordance with the present teachings may be provided with protrusion ring of a different angular extent than that shown in FIGS. 23-26 or with a plurality of protrusion rings spaced from each other around the internal peripheral surface of the temporary coping. Those having ordinary skill in the art would recognize various modifications to the protrusion features that could be made without departing from the scope of the present teachings. As used herein, when referring to a "protrusion ring," it should be understood that such terminology is intended to cover partial (e.g., arc-shape) protrusion structures. The term protrusion ring is not limited to protrusion features that extend around an entire inner peripheral surface (such as, for example, 360°), but can include continuous protrusions that have various lengths (or angular extent).

The configuration (e.g., size and shape) of the protrusions features, whether in the form of one or more protrusion rings or one or more relatively localized protrusions, may be chosen based on the various considerations, such as, for example, the shape and size of one or more retention grooves with which the protrusion features are designed to engage, the desired force required to achieve a mating engagement, e.g., snap-fit engagement, between the protrusion features and the retention grooves, and/or the retention force desired between the abutment and temporary coping. Likewise, the number and positioning of the protrusion features, whether in the form of protrusion rings or relatively localized protrusions, may vary and may be selected based on similar considerations; the number of protrusion features on the temporary coping may range from one to more than one.

In various exemplary embodiments, the protrusion features, whether in the form of a continuous ring and/or localized protrusions, may have a substantially convex profile with a radius of curvature ranging from about 0.015 in. to about 0.025 in., for example, about 0.02 in., and may protrude from the internal peripheral surface portion of the coping from about 0.002 in. to about 0.006 in., for example, about 0.004 in. The height of the protrusion features (e.g., as measured along the longitudinal axis direction of the temporary coping) may range from about 0.015 in. to about 0.040 in., for example about 0.021 in. Of course, those having ordinary skill in the art would understand that these dimensions are exemplary only and may vary depending on, for example, the dimensions of a retention groove with which the protrusion features are designed to engage in a snap-fit manner, the desired retention force between the protrusion features and such a retention groove, etc. By way of example, the one or more protrusion features on a temporary coping in accordance with various exemplary embodiments may be configured so as to provide substantially a 100% interference mating fit with a corresponding retention groove on an abutment with which the one or more protrusion features are desired to engage. By way of further example, the one or more protrusion features on a temporary coping may be configured so as to provide a force ranging from about 2.5 lb. to about 7 lb. to achieve a mating engagement, for example, via a snap-fit, with one or more retention grooves. In addition, the one or more protrusion features on a temporary coping may be configured so as to provide a force ranging from about 10 lb. to about 20 lb., for example, about 15 lb., to disengage the protrusions from one or more retention grooves on an abutment (i.e., pull off the temporary coping from the abutment).

In another exemplary embodiment (not shown), a temporary coping may be substantially the same as the temporary coping 800 or 2700 with the exception of not being provided with a flat surface portion 820, 2720. In the case of such a temporary coping, the protrusion ring may extend around the entire internal peripheral surface of the temporary coping. Such a temporary coping without the flat surface portion 820 (often referred to as a "round" temporary coping, whereas a temporary coping with the flat surface portion is often referred to as a "flat" temporary coping) is typically used when multiple restorations are required in a patient's mouth. Those ordinarily skilled in the art are familiar with the use of a pair of so called "round" temporary copings used in the context of multiple restorations.

In various exemplary embodiments, temporary copings in accordance with the present teachings may be made of a plastic material that relatively easily permits mating engagement (e.g., via snap-fit engagement) of one or more protrusion features with one or more retention grooves on an abutment. Examples of suitable materials include, but are not limited to, materials comprising poly-ether-ether ketone (PEEK), hybrid PEEK, PEEK polymer, nylon, and/or Delrin. Alternatively, temporary copings in accordance with the present teachings may be made of a metal material, such as, for example, various grades of titanium and titanium alloys. Yet another suitable material for temporary copings in accordance with the present teachings may include a hybrid composite material comprising both metal and plastic.

Various exemplary materials, such as, for example, a bis-acrylic material, that permit a chemical bonding of the temporary coping with a temporary replacement tooth veneering material also may be used to form temporary copings in accordance with exemplary embodiments of the present teachings. Such chemical bonding may be used without the need for another bonding mechanism to bond the temporary coping to the temporary replacement tooth veneering material (e.g., acrylic material and/or other material suitable for forming a temporary restoration with which those having ordinary skill in the art have familiarity), although additional bonding mechanisms may be employed. For various materials that may be used to make a temporary coping that achieves such a chemical bonding with the temporary restoration, reference is made to U.S. patent application Ser. No. 12/332,524, filed Dec. 11, 2008, which is incorporated by reference herein in its entirety. As set forth in U.S. patent application Ser. No. 12/332,524, incorporated by reference herein, the term "chemical bond," and variations thereof, refers to a chemical bond between the material of the temporary coping and the material of the restorative tooth. A chemical bond according to the present teachings refers to a direct bond between the materials forming the chemical bond, for example, without an adhesive between the two materials and without relying on a mechanical engagement of cooperating structures to form the bond. Materials that are chemically bonded are fused together by molecular bonds. One example of a suitable bis-acrylic material that may be used to form a temporary coping in accordance with various exemplary embodiments includes Protemp™ Plus Temporization Material made by 3M.

In order to construct a permanent restoration, various exemplary embodiments of the present teachings also contemplate the use of an analog having substantially the same coronal portion configuration (e.g., component supporting portion) as that of exemplary embodiments of abutments of the present teachings. For example, with reference to the abutment 100 of the exemplary embodiment of FIGS. 1-5, an exemplary embodiment of the analog in accordance with the present teachings presents a configuration having the same configuration as component supporting portion 150, retention groove 125 and the upper part of frustoconical portion 140 (i.e., from the retention groove 125 to the widest portion $D_a$ of the abutment 100 before the portion 140 begins to taper toward the shoulder 130. Exemplary embodiments of analogs in accordance with the present teachings may be used, for example, in a dental laboratory, and may be configured to engage with the one or more burnout copings to which wax may be applied to perform a "lost wax" technique which results in melting of the burnout coping (as described above) to form a permanent restoration framework. In an alternative exemplary embodiment in accordance with the present teachings, wax may be applied directly to the analog, without using a burnout coping, and a "lost wax" technique performed on the so-formed wax mold to produce a framework. In some cases, waxing directly to an analog may provide more precise dimensions than can be obtained when using a burnout coping due to the burnout coping being an injection-molded part that may take up some additional room when pouring the molten material to form the framework. In the context of applying wax directly to an analog, it is also contemplated that a cuff portion of the burnout coping may be provided on the analog and wax applied to the analog directly as well as the cuff portion thereon, which may be used to achieve a desired apical end finish line of the ultimate framework without the need to form the wax to mimic the desired finish line portion of the framework.

FIGS. 28-30 show an exemplary embodiment of an analog in accordance with the present teachings. As illustrated in those figures, the analog 2800 includes a tapered component supporting portion 2850 having a flat side portion 2820 that is configured substantially the same as the corresponding portion 150 and flat side portion 120, respectively, of the abutment 100, with the exception of the analog not being provided with the opening 115 or groove 135 that are configured to receive tools for torquing the analog. The analog 2800 also includes at least one retention groove 2825 that is dimensioned and positioned substantially the same as the retention groove 125 on the abutment 100, and a portion 2841 that flares outwardly slightly in an apical direction adjacent the retention groove 125 before meeting a shoulder portion 2842 configured to mimic the shoulder on an implant, or in alternative exemplary embodiments such as FIG. 40, on an abutment.

Thus, in accordance with various exemplary embodiments of the present teachings, an analog, such as analog 2800, may present dimensions and a configuration for the component supporting portion, including one or more retention grooves, and portion just apical to the retention groove up to a shoulder portion provided on the analog that substantially correspond to those same portions on an abutment in accordance with the present teachings. Various exemplary dimensions and configurations, and modifications thereto, have been described above with reference to the abutment 100 of the exemplary embodiments of FIGS. 1-5 and those dimensions, configurations, and modifications are applicable to the corresponding parts of the analogs according to exemplary embodiments of the present teachings, including, for example, analog 2800.

As mentioned above, in one exemplary technique for forming a framework of a permanent restoration, a burnout coping may be used that fits to an analog in accordance with the present teachings (such as, e.g., analog 2800) in order to form a wax mold therefrom. The burnout copings also can include both so-called "flat" (i.e., including the flat internal surface portion) and "round" (i.e., without the flat internal surface portion) configurations, with "flat" burnout copings being used for single restorations and "round" being used for multiple restorations. The burnout copings may also include various protrusion feature configurations as described above with reference to the temporary copings may be used to provide a mating engagement, for example, a snap-fit engagement, with the retention groove 2825 of the analog in a manner substantially similar to that described above with reference to the temporary copings' engagement with abutments in accordance with exemplary embodiments of the present teachings.

Figure 31:
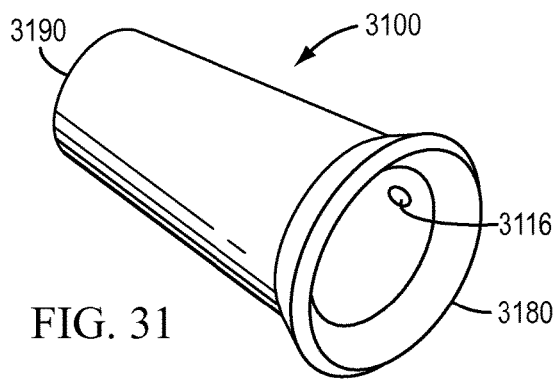
FIG. 31 is a perspective view of an exemplary embodiment of a burnout coping in accordance with the present teachings.
Figure 32:
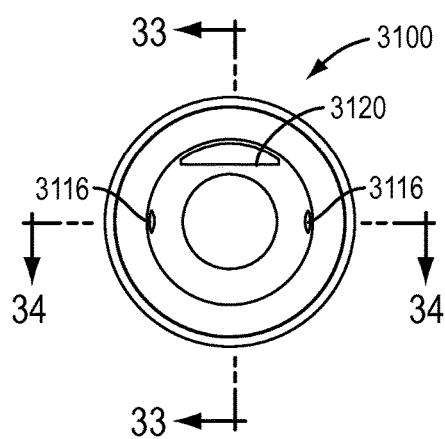
FIG. 32 is an apical end view of the burnout coping of FIG. 31.
Figure 33:
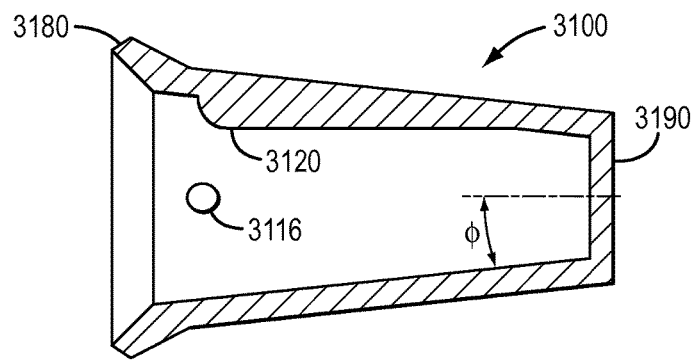
FIG. 33 is a cross-sectional view of the burnout coping of FIG. 31 taken through line 33-33 in FIG. 32.

FIGS. 31-34 show one exemplary embodiment of a burnout coping 3100 in accordance with the present teachings. The burnout coping 3100 has a tapered (e.g., frustoconical), hollow configuration having an open apical end 3180 and a closed coronal end 3190. The burnout coping 3100 is configured to be advanced over an analog, such as, for example, analog 2800. As shown best in FIGS. 32-34 (FIG. 32 being an end view taken form the apical end in FIG. 31; FIG. 33 being a cross-sectional view taken through line 33-33 in FIG. 32; and FIG. 34 being a cross-sectional view taken through line 34-34 in FIG. 32), provided on the internal surface of the burnout coping 3100 proximate the apical end 3180 are protrusion features in the form of two localized protrusions 3116 disposed substantially opposite to each other (180° apart) around the inner peripheral surface of the coping 3100. Similar to protrusion features on the transfer coping, as described above, the protrusions 3116 may be configured to engage one or more retention grooves provided on an analog, such as, for example, the retention groove 2825 on the analog 2800. The protrusions 3116 may have a convex profile and be configured to engage in a snap-fit manner with one or more retention grooves, e.g, groove 2825, on an analog so as to form an accurate and secure retention of the burnout coping 3100 and the analog.

As best shown in FIGS. 32 and 33, an internal flat surface portion 3120 of the burnout coping 3100 may extend inwardly relative to the remaining surface portions. In a manner similar to that described above with reference to other components herein, the flat surface portion 3120 may present a substantially flat surface facing toward a center of the burnout coping 3100, and may be configured to correspond and abut in a substantially flush manner with a flat surface portion on an analog, for example, flat surface portion 2820 on analog 2800.

Figure 34:
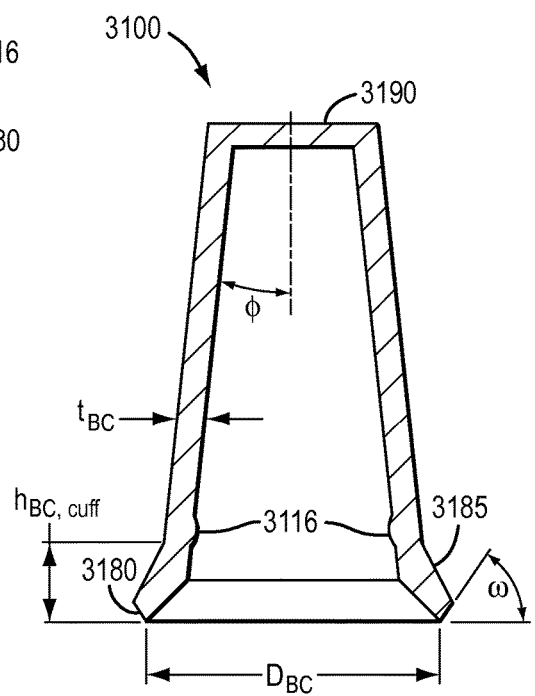
FIG. 34 is a cross-sectional view of the burnout coping of FIG. 31 taken through line 34-34 in FIG. 32.

As is perhaps best shown in FIGS. 33 and 34, the interior of the burnout coping 3100 may present a tapered surface from the apical open end 3180 toward the coronal end 3190, and the degree of taper may substantially correspond to the taper of the coronal portion of an analog with which the burnout coping 3100 is configured to engage, such as, for example, portion 2850 of analog 2800. For example, the angle of taper, $\phi$, may range from about 4° to about 8°, for example, from about 5.5° to about 6.5°, for example, $\phi$ may be about 6°. The length and other dimensions of the burnout coping 3100 may be selected as desired based on the implant and analog dimensions and the desired dimensions of the framework that will ultimately be formed using the burnout coping 3100. By way of nonlimiting example, burnout copings may be configured to ultimately produce frameworks that are configured to fit with implants having coronal neck diameters ranging from about 2.6 mm to about 7 mm, for example, about 4.1 mm, about 4.8 mm or about 6.5 mm. Thus, the diameter $D_{BC}$ (see FIG. 34) may range from about 2.6 mm to about 7 mm, for example, $D_{BC}$ may be about 4.1 mm, about 4.8 mm, or about 6.5 mm, or sized within a range as described above if platform sizing is desirable.

The burnout coping 3100 also may include a cuff 3185 at the apical end 3180 having a height $h_{BC, \, cuff}$ ranging from about 0.3 mm (0.012 in.) to about 0.5 mm (0.020 in.), and the overall length of the burnout coping from the apical end 3180 to coronal end 3190 may range from about 4 mm to about 9 mm. The angle $\omega$ of the outer surface at the end 3180 of the cuff 3185 may range, for example, from about 45° to about 75°, for example, $\omega$ may be about 60°. In various exemplary embodiments, the thickness $t_{BC}$ of the walls of the burnout coping 3100, except at the location of the flat surface portion 3120, if any, may range from about 0.012 in. to about 0.02 in.

The beveled (e.g., angled) surfaces at the apical end 3180 of the cuff 3185 may provide a surface similar in shape to what is desired for the ultimate framework formed therefrom so as to provide a continuous emergence profile of a permanent restoration from where it mates with an implant shoulder (e.g., shoulder 1050 of implant 1000) or alternatively with a shoulder on an abutment (e.g., shoulder 4105 in FIG. 41) in various exemplary embodiments. An internal beveled surface defining the apical opening of the burnout coping apical end 3180 may be configured to abut in a flush mating manner with a shoulder provided on an analog (such as, e.g., shoulder 2842 in FIGS. 28 and 29) when the burnout coping 3100 is retained on the analog.

Although the exemplary embodiment of FIGS. 31-33 show a burnout coping provided with two opposing localized protrusions 3116, those having ordinary skill in the art would recognize that any number of such localized protrusions ranging from one to more than one may be provided and positioned as desired around the periphery of the burnout coping in order to provide a secure and accurate mating engagement (e.g., a snap-fit engagement) with one or more retention grooves on an analog in accordance with the present teachings. Moreover, in an alternative exemplary embodiment, in lieu of localized protrusions, a protrusion ring similar to protrusion ring 816 of the temporary coping 800 described above may be provided. With the exception of the wall thickness, a burnout coping provided with such a protrusion ring would have a similar cross-section as that shown in FIG. 24. In yet further alternative exemplary embodiments (not shown), rather than a single protrusion ring, a burnout coping in accordance with the present teachings may be provided with a protrusion ring of a different angular extent than that shown in FIG. 24 or with a plurality of protrusion rings spaced from each other around the internal peripheral surface of the temporary coping at substantially the same location along a length of the temporary coping. Those having ordinary skill in the art would recognize various modifications to the protrusion features that could be made without departing from the scope of the present teachings.

The configuration (e.g., size and shape) of the protrusion features, whether in the form of one or more protrusion rings or one or more relatively localized protrusions, may be chosen based on various considerations, including the degree of engagement and accurate secure fit provided with a retention groove on an analog and/or the ability to provide a secure and/or accurate retention of a permanent restoration framework formed from such a burnout coping on an abutment, as will be described in further detail below. In various exemplary embodiments, the protrusion features, whether in the form of one or more continuous rings and/or localized protrusions, may have a substantially convex profile with a radius of curvature ranging from about 0.015 in. to about 0.025 in., for example, about 0.02 in., and may protrude from the internal peripheral surface portion of the coping from about 0.003 in. to about 0.006 in., for example, about 0.004 in. The dimension of the protrusion features measured along the longitudinal axis of the burnout coping (i.e., the height) may be substantially the same as the height (e.g., height $h_g$) of a retention groove with which the protrusion features are configured to mate and may in exemplary embodiments range from about 0.021 in. to about 0.0492 in.

Of course, those having ordinary skill in the art would understand that the dimensions above are exemplary only and may vary depending on, for example, the dimensions of a retention groove with which the protrusion features are designed to engage, the desired retention force between the protrusion features and such a retention groove, etc. For a burnout coping, the desired retention force may be a force that is sufficient to permit wax to be applied to the burnout coping without the burnout coping being removed from the analog. By way of example, the one or more protrusion features on a burnout coping may be configured such that a force ranging from about ½ lb. to about 2 lb., for example, about 1 lb., can be applied to achieve engagement of the one or more burnout coping protrusion features with one or more retention grooves on an analog.

In another exemplary embodiment (not shown), a burnout coping may be substantially the same as the burnout coping 3100 with the exception of not being provided with a flat surface portion 3120. In the case of such a burnout coping, if a protrusion ring is provided instead of localized protrusion, in an exemplary embodiment, such ring may extend around the entire internal peripheral surface of the burnout coping (i.e., 360°). Such a burnout coping without the flat surface portion 3120, i.e., a "round" burnout coping, is typically used when multiple restorations are required in a patient's mouth and a framework configured for multiple restorations is desired. Those ordinarily skilled in the art are familiar with the use of a pair of so called "round" burnout copings used in the context of multiple restorations.

In various exemplary embodiments, burnout copings in accordance with the present teachings may be made of a plastic material that permits melting of the burnout coping during pouring of the molten material during the "lost wax" molding technique. Those having ordinary skill in the art are familiar with various materials suitable for making burnout copings that could be used with exemplary burnout copings of the present teachings.

Providing burnout coping (e.g., both flat and round) and analog configurations that are substantially the same and designed to mimic the shape and dimensions of the temporary copings and abutments, respectively, of the exemplary embodiments described above, may serve a variety of purposes. For example, when producing a framework for a permanent restoration (whether single or multiple), the framework may be sized and configured to provide an accurate mating engagement with an abutment, as opposed to being relatively large and loose-fitting relative to the abutment, which can occur if the analog is slightly oversized relative to the abutment, as some conventional analogs are designed in order to, for example, account for hydraulic pressure when using cement to secure the framework to an abutment. This enhanced accuracy in the fit between the framework and the abutment can be achieved whether a burnout coping is utilized or wax is formed directly around the analog without the use of a burnout coping to form the mold for the "lost wax" production of the framework. Further, this more conforming and accurate fit between the framework and the abutment may be achieved in part because the one or more retention grooves provided on the abutment may provide a region in which excess bonding material (e.g., cement) may be collected during seating of the replacement tooth on the implant in instances wherein frameworks are machined to remove any protrusions formed on internal surfaces thereof as a result of molding using burnout copings and/or analogs in accordance with exemplary embodiments. Thus, a reduction in hydraulic pressure associated with seating a replacement tooth formed by using the various components in accordance with exemplary embodiments of the present teachings may occur, and therefore, an oversized replacement tooth is not needed to accommodate the bonding material to alleviate excessive hydraulic pressures.

In various exemplary embodiments, which will be discussed in more detail below, it may not be necessary to perform any machining, or at least minimal machining so as to achieve mating engagement of the protrusion features ultimately formed on a framework made from wax molds of either the burnout copings or analogs in accordance with exemplary embodiments of the present teachings. However, in the event that it is desirable to remove any formed protrusion features altogether from a framework, use of a burnout coping configuration that includes protrusion features on an internal peripheral surface portion, e.g., like protrusions 3116 shown in FIGS. 31-34, that are configured to engage with one or more retention grooves on an analog eliminates the need to machine off a portion, such as a lip, extending from an end of a framework that is cast from the burnout coping. Elimination of such an end structure that needs to be machined off may ensure a more accurate fit between the framework and the analog and/or the abutment with which the framework ultimately engages. Overall, improving the accuracy of the fit may reduce the risk of undesired stress on, and potential failure of, the replacement permanent tooth due to improper seating of the framework relative to the abutment and/or may reduce the risk of cement washout (if cement bonding is desired) during placement of the permanent replacement tooth.

Moreover, although it may be desirable in some cases to remove (e.g., machine) protrusion features formed on an internal peripheral surface of a framework produced from a burnout coping having one or more corresponding protrusion features and/or from a wax mold formed directly on an analog presenting a retention groove, removing such protrusion features may be relatively easy because one may relatively easily machine such a protrusion to the level of the inner surface on which the protrusion is disposed. To the contrary, machining a structure disposed at the end of the framework, such as, a lip, for example, may be more time-consuming and may lead to a less accurate structure because it may be difficult to determine how much of the extending structure needs to be machined. Overall, therefore, the use of a burnout coping structure in accordance with exemplary aspects of the present teachings may enhance the accuracy of the fit between the framework and an abutment and/or an analog, and may reduce the amount of time needed to produce a replacement tooth.

As mentioned above, in various exemplary embodiments, a framework for a permanent restoration may be configured for engagement with and retention on a grooved abutment (or multiple grooved abutments in the case of multiple restorations) without the need for using cement or other bonding material to bond the framework to the abutment. In various exemplary embodiments as described herein, such a framework may be formed via a "lost wax" technique using either a burnout coping in accordance with exemplary embodiments of the present teachings (i.e., provided with one or more protrusion features on an internal peripheral surface thereof) or a direct wax approach in which wax is applied directly to a grooved analog in accordance with exemplary embodiments of the present teachings. Further, in various exemplary embodiments, the present teachings contemplate frameworks that include one or more protrusion features on an internal peripheral surface thereof that are configured to engage with an abutment having one or more retention grooves similar to the manner in which impression and/or temporary copings described above engage with a grooved abutment in accordance with the present teachings. The one or more protrusion features provided on a framework in accordance with various exemplary embodiments of the present teachings may be in the form of any of the protrusion features described herein with reference to the impression, temporary and burnout copings above.

By way of example, when wax is formed directly on an analog, such as analog 2800, and a "lost wax" technique performed on that wax mold to create a framework, the wax mold, and thus the framework, will be formed with a protrusion ring on an internal surface corresponding substantially to the retention groove 2825 on the analog 2800. Likewise, when a burnout coping with one or more protrusion features on an internal surface thereof configured to engage in a snap-fit manner with an analog, as described above in accordance with exemplary embodiments of the present teachings, is used to perform a "lost wax" technique, the framework produced therefrom will also include corresponding protrusion features on its internal surface. Rather than entirely machining off such protrusion features, however, various exemplary embodiments of the present teachings contemplate utilizing the protrusion features formed on the framework to provide a mating engagement of the protrusion features with one or more retention grooves on an abutment (such as, for example groove 125 on abutment 100). In various exemplary embodiments, the mating engagement between the one or more protrusion features on a framework and the one or more retention grooves on an abutment may be a snap-fit engagement.

Figure 35:
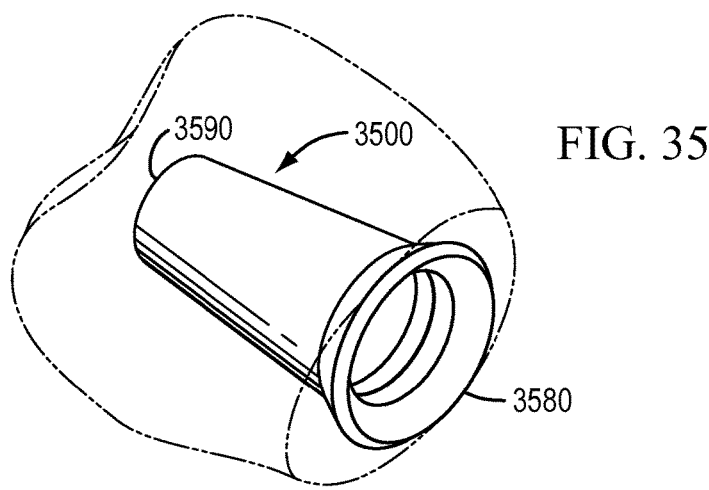
FIG. 35 is a perspective view of an exemplary embodiment of a framework supporting veneering material (shown in dashed lines so as to see the framework structure) to form a permanent restoration in accordance with the present teachings.
Figure 36:
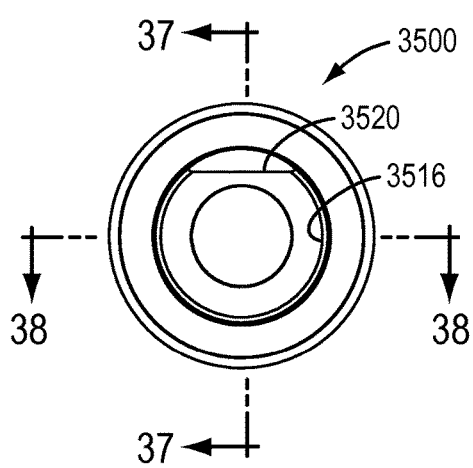
FIG. 36 is an apical end view of the framework of FIG. 35.
Figure 37:
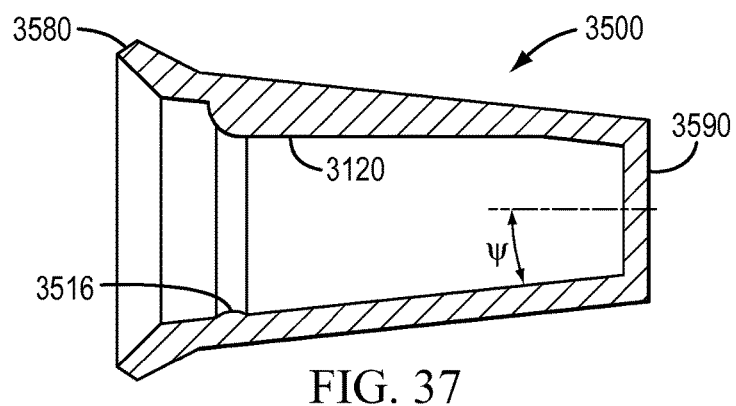
FIG. 37 is a cross-sectional view of the framework of FIG. 35 taken through line 37-37 in FIG. 36.

FIGS. 35-38 illustrate one exemplary embodiment of a framework 3500 in accordance with the present teachings. In FIG. 35, the framework 3500 is shown for illustrative purposes supporting veneering material shaped to form a tooth to provide a schematic depiction of an exemplary embodiment of a permanent final restoration. The framework 3500 has a tapered (e.g., frustoconical), hollow configuration having an open apical end 3580 and a closed coronal end 3590. The framework 3500 is configured to be advanced over an abutment, such as, for example abutment 100. As shown best in FIGS. 36-38 (FIG. 36 being an end view of the framework 3500 taken from the apical end in FIG. 35; FIG. 37 being a cross-sectional view of the framework 3500 taken through line 37-37 in FIG. 36; and FIG. 38 being a cross-sectional view of the framework taken through line 38-38 in FIG. 36), provided on the internal surface of the framework 3500 proximate the apical end 3580 is a protrusion ring 3516 that extends about 270° around the internal peripheral surface of the framework 3500. Similar to various other protrusion features described herein, the protrusion ring 3516 may be configured to matingly engage one or more retention grooves provided on an abutment, such as, for example, the retention groove 125 on the abutment 100, in accordance with exemplary aspects of the present teachings. The protrusion ring 3516 may have a convex profile and be configured to matingly engage, for example, via snap-fit engagement, with a groove, e.g, groove 125, on an abutment so as to form an accurate and secure retention of the framework 3650 (and thus a permanent restoration) and the abutment.

As best shown in FIGS. 36 and 37, the framework 3500 may comprise an internal flat surface portion 3520 that extends inwardly relative to the remaining surface portions. In a manner similar to that described above with reference to other components herein, the flat surface portion 3520 may present a substantially flat surface facing toward a center of the framework 3500, and may be configured to correspond and abut in a substantially flush manner with a flat surface portion on an abutment, for example, flat surface portion 120 on abutment 100.

Figure 38:
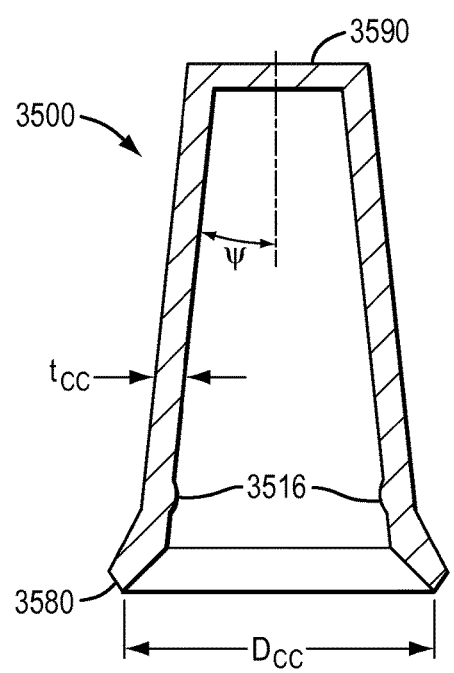
FIG. 38 is a cross-sectional view of the framework of FIG. 35 taken through line 38-38 in FIG. 36.

As is perhaps best shown in FIGS. 37 and 38, the interior of the framework 3500 may present a tapered surface from the apical open end 3580 toward the coronal end 3590, and the degree of taper may substantially correspond to the taper of the component supporting portion of an abutment with which the framework 3500 is configured to engage, such as, for example, component supporting portion 150 of abutment 100. For example, the angle of taper, $\Psi$, may range from about 4° to about 8°, for example, from about 5.5° to about 6.5°, for example, $\Psi$ may be about 6°. The length and other dimensions of the framework 3500 may be selected as desired based on the implant and abutment dimensions with which the framework is designed to engage to provide the permanent restoration. By way of non-limiting example, as with the temporary coping described above, the framework 3500 may be configured to fit with implants having a coronal neck diameter ranging from about 2.6 mm to about 7 mm, for example, about 4.1 mm, about 4.8 mm or about 6.5 mm coronal neck diameters. And the apical end 3580 may be configured to form a flush mating engagement with a shoulder of such implants, although platform sizing may be used to alter the lateral extent of the apical end 3580 relative to the implant shoulder. Thus, $D_{CC}$ (see FIG. 38) may in exemplary embodiments range from about 2.6 mm to about 7 mm. For example, $D_{CC}$ may be about 4.1 mm, about 4.8 mm, or about 6.5 mm, or may fall within the ranges described above with respect to the description of platform sizing when such platform sizing is desired.

In various exemplary embodiments, internal dimensions (such as, for example, the diameter and length) of the framework 3500 may be selected so as to provide a substantially flush mating surface contact (i.e., within machining tolerances) between the internal peripheral surfaces of the framework 3500 and the outer peripheral surfaces of the component supporting portion of an abutment (e.g., portion 150 of abutment 100) with which the framework 3500 is configured to engage.

In an alternative exemplary embodiment, the apical end of the framework may be configured to engage with a shoulder provided on an abutment (e.g., shoulder 4105 on abutment 4100 in FIG. 41).

As shown in FIGS. 35, 37, and 38 the apical end 3580 may include beveled (e.g., angled) surfaces in order to provide a flush mating engagement with a shoulder on an implant or abutment so as to provide a smooth emergence profile of the permanent restoration off of the implant.

Although the exemplary embodiment of FIGS. 35-38 show a framework provided with a single protrusion ring extending around an internal peripheral surface up to the flat surface portion 3520, in an alternate exemplary embodiment (not shown), a framework 3500 may be provided with one or more relatively localized protrusions (not shown) configured to engage with one or more retention grooves on an abutment in accordance with the present teachings. For example, the framework 3500 may include two localized protrusions disposed substantially opposite one another with the internal flat surface portion 3520 being disposed substantially midway between the two protrusions, in a manner similar to that illustrated in the view of the exemplary embodiment of the temporary coping of FIG. 27. Other portions of the framework may be substantially the same as those described. In yet another alternative exemplary embodiment (not shown), rather than a single protrusion ring, a framework in accordance with the present teachings may be provided with a protrusion ring of a different angular extent than that shown in FIGS. 35-38 or with a plurality of protrusion rings spaced from each other around the internal peripheral surface. Those having ordinary skill in the art would recognize various modifications to the protrusion features of frameworks, including modifications as described above with reference to protrusion features of other components, that could be made without departing from the scope of the present teachings.

The configuration (e.g., size and shape) of the protrusion features, whether in the form of, for example, one or more protrusion rings or one or more relatively localized protrusions, may be chosen so as to provide a secure, mating engagement, such as, for example, via snap-fit engagement, with one or more retention grooves on an abutment with which the framework is designed to engage. Likewise, the number and positioning of the protrusions, whether in the form of, for example, protrusion rings or relatively localized protrusions, may vary and may be selected based on various considerations similar to those described above with reference to the protrusion features on temporary copings in accordance with exemplary embodiments of the present teachings; the number of protrusion features on the frameworks may range from one to more than one.

Depending on the dimensions of either a retention groove on an analog (when a direct wax technique is used) or protrusion features on a burnout coping (when a burnout coping wax technique is used), in some exemplary embodiments, the present teachings contemplate that the corresponding protrusion feature(s) formed on the inner peripheral surface of the framework may be machined somewhat to reduce the extent to which the protrusion features extend in order to form a desired mating engagement with one or more retention grooves on an abutment. By way of non-limiting example only, the final dimensions of the one or more protrusion features on a framework, whether formed with no machining occurring or some machining occurring as needed, may have a substantially convex surface profile with a radius of curvature ranging from about 0.0008 in. to about 0.0018 in., for example, from about 0.0105 in. to about 0.0013 in., and may protrude from the internal peripheral surface portion of the coping from about 0.0001 in. to about 0.004 in., for example, about 0.002 in. to about 0.003 in. The dimension of the protrusion features as measured along the longitudinal axis direction of the framework (i.e., the height of the protrusion features) may range from about 0.0008 in. to about 0.028 in., for example, from about 0.0011 in. to about 0.015 in.

Of course, those having ordinary skill in the art would understand that these dimensions are exemplary only and may vary depending on, for example, the dimensions of a retention groove with which the protrusion features are designed to engage in a mating manner, the desired retention force between the protrusion features and such a retention groove, etc. By way of example, the one or more protrusion features may be configured such that a force ranging from about ½ lb. to about 20 lb., for example, from about 5 lb. to about 20 lb., is sufficient to achieve the mating engagement (e.g, a snap-fit engagement) of the one or more protrusion features on the framework with one or more retention grooves on an abutment. Also by way of non-limiting example, the protrusion feature dimensions may be such that the framework may be pulled off of the abutment (i.e., the one or more protrusion features disengaged from the one or more retention grooves on the abutment) under a force ranging from about 1 lb. to about 1.5 lb. prior to an enhanced retention of the framework on the abutment resulting from saliva, etc. working to form a seal between the abutment and the framework as is discussed in more detail below.

In another exemplary embodiment (not shown), a framework may be substantially the same as the framework 3500 with the exception of not being provided with a flat surface portion 3520. In such a case, the protrusion ring may extend around the entire internal peripheral surface of the framework. A pair of such frameworks without the flat surface portion 3520 is typically used when multiple restorations are required in a patient's mouth. Those ordinarily skilled in the art are familiar with the use of a pair of so called "round" (typically used for bridges) frameworks for use in the context of multiple restorations.

In various exemplary embodiments, frameworks to be secured relative to implants in accordance with the present teachings may be made of a various biocompatible metals or biocompatible metal alloys, such as, for example, a semi-precious noble metal alloy. One exemplary suitable metal alloy that may be used comprises about 60% to about 70% palladium and less than about 15% silver. Another suitable material from which the frameworks may be made includes zirconium, e.g., zirconium composites or alloys.

Suitable exemplary materials also may comprise various biocompatible ceramics. Thus, although various exemplary embodiments above describe a "lost wax" casting procedure to form a metal framework, such a technique is exemplary and non-limiting. In this regard, the present teachings also contemplate the use of milling and/or other machining techniques to form frameworks in accordance with exemplary embodiments of the present teachings. In such techniques, a scan of the abutment attached to an implant in a patient's mouth may be taken and a framework milled to the configuration (e.g., shape and dimensions) obtained from the scan so that a framework provided with one or more protrusion features may be made that are configured for mating engagement, such as via a with snap-fit retention to the abutment. Those having ordinary skill in the art are familiar with various materials suitable for making frameworks, with the technique for making such frameworks varying depending on the material chosen.

Thus, in accordance with various exemplary embodiments of the present teachings, frameworks used for permanent restorations to be secured relative to dental implants may be configured to provide a snap-fit, secure and accurate engagement with an abutment including one or more retention grooves in accordance with exemplary embodiments of the present teachings. As with temporary copings and impression copings in accordance with exemplary embodiments of the present teachings, and as described herein, the frameworks may further be configured to form a finish line with an implant shoulder similar to the finish line S shown in FIGS. 22A and 22B. The snap-fit engagement of the frameworks in accordance with exemplary embodiments with the abutments in accordance with exemplary embodiments may permit a permanent restoration to be secured relative to a dental implant without the need for cement or other type of adhesive bonding.

Moreover, while not wishing to be bound by any particular theory, the inventors of the present application believe that once a framework that includes one or more protrusion features that are engaged with one or more corresponding retention grooves on an abutment in accordance with the present teachings, over a period of time saliva from the mouth of a patient in which the abutment and framework are implanted may enhance the seal between the framework and the abutment, helping to ensure a secure and long-lasting engagement so as to be sufficient to support a permanent replacement tooth. Additionally, tissue growth around the framework may also enhance the retention of the framework on the abutment. After such a time period has passed to permit saliva and/or tissue growth to enhance the retention of the framework on the abutment, in accordance with various exemplary embodiments, the force required to lift the framework off of the abutment may range from about 20 lb. to about 30 lb.

Although various exemplary embodiments have been described herein with reference to the use with an implant having a shoulder that provides a finish line for the apical ends of components engaged with an abutment secured to the implant, in some cases, the shoulder of the implant may not be easily accessible when securing a component to the abutment. For example, in some cases, the implant may be submerged below the bone (e.g., a dual-stage implant), or a patient may have a thick tissue margin that covers a shoulder of the implant (e.g., a tissue margin greater than or equal to about 3 mm). In such circumstances, therefore, the present teachings contemplate an abutment that includes a shoulder with which the apical ends of components snap-fitting thereto can mate to provide the finish line. An exemplary embodiment of an abutment 4100 having a shoulder 4105 is depicted in FIG. 41. As shown, the abutment 4100 may include a gingival cuff 4145 between the implant engaging portion 4140 and the component supporting portion 4150. The length of the gingival cuff from the implant engaging portion 4140 to the component supporting portion 4150 may range from about 1 mm to about 4 mm. A shoulder 4105 may be positioned at a coronal end of the gingival cuff 4145 slightly below the retention groove 4125. The shoulder 4105 may be angled in a manner similar to the shoulder 1050 on the implant 1000, and various components described herein may have apical ends providing angled surfaces configured to result in a flush mating contact with the shoulder 4105. The end of the gingival cuff 4145 opposite the shoulder 4105 may be provided with an angled surface configured to mate in a flush contacting manner with a shoulder on an implant (e.g., shoulder 1050 on implant 1000) with which the abutment 4100 engages. Other portions of the abutment 4100 may be substantially the same as the abutment 100 and therefore are not described.

Also, although various exemplary embodiments of the present teachings described herein utilize a snap-fit engagement between one or more protrusion features and one or more retention grooves, it is envisioned that the mating engagement between such protrusion features and retention grooves may include various interference fits sufficient to achieve the desired retention of a component comprising such protrusion features on an abutment comprising such retention grooves. Thus, it should be understood by those ordinarily skilled in the art that the retaining mating engagement between protrusion features and retention grooves in accordance with various exemplary embodiments of the present teachings may not necessarily result in an audible and/or tactile "snap" when engagement of those parts occurs.

Although various exemplary embodiments described herein have been described as configured to be used with dental implants, it is envisioned that the various components in accordance with the present teachings may be configured for use with other types of bone and/or cartilage implants, including, for example, extra-oral and/or orthopedic implants, for which it may be desirable to take an impression. Examples of extra-oral implants may include, for example, implants used for prosthetic eyes, ears, or noses.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the written description and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the devices and methods of the present disclosure without departing from the scope its teachings. By way of example, various dimensions, shapes, materials, and/or arrangements of parts may be altered based on desirable features and/or applications, and those having ordinary skill in the art would recognize how to make such modifications in light of the present teachings. By way of example, although in the exemplary embodiments shown and described above, the protrusion features, whether localized or in the form of protrusion rings, had generally radial profiles (e.g., semi-spherical), those having ordinary skill in the art that would understand that various shapes and configurations of protrusion features, including but not limited to, for example, rectangular, cubical, pyramidal, etc. may be used without departing from the scope of the present teachings. In addition, although in the exemplary embodiments above, various retention grooves are shown and described as radiused grooves having a substantially arc-shaped profile, those having ordinary skill in the art would understand that such grooves could have a variety of shapes, including, but not limited to, for example, notch-shaped (e.g., V-shaped), or presenting multiple sides.

Further, those having ordinary skill in the art would understand that angled abutments, such as depicted in FIG. 39, for example, may be provided, and corresponding component parts altered as desired to cooperate with such angled abutments.

In the exemplary embodiments described above, various features have been discussed. Those having ordinary skill in the art would recognize that in some cases, features described with respect to one exemplary embodiment may be combined and/or used in conjunction with another exemplary embodiment even if not specifically described herein. The present teachings are intended to cover such modifications and combinations as would be apparent to those ordinarily skilled in the art.

The various exemplary embodiments described and shown herein are not intended to limit the present teachings. To the contrary, the present teachings are intended to cover alternatives, modifications, and equivalents. Other embodiments of the present teachings will be apparent to those skilled in the art from consideration of the specification and practice of the present teachings disclosed herein. It is intended that the specification and exemplary embodiments be considered as exemplary only, with the claims being provided a scope of a breadth supported by the present teachings.

What is claimed is:

1. A system for dental restorations, the system comprising:
an abutment comprising an implant engaging portion and a component supporting portion terminating in a coronal end of the abutment,
wherein the implant engaging portion and the component supporting portion are a single-piece structure,
wherein the implant engaging portion extends apically from the component supporting portion and has an external surface feature configured to be received in mating engagement within an opening in a dental implant, and
wherein the component supporting portion comprises at least one first snap-fit retention feature disposed on an outer peripheral surface of the component supporting portion, the at least one first snap-fit retention feature being located at an axial location along the component supporting portion proximate to a location where the implant engaging portion meets the component supporting portion; and
a temporary coping having a frustoconical shape,
wherein the temporary coping is made from a material that permits chemical bonding of the temporary coping with a veneering material of a temporary tooth restoration, and
wherein the temporary coping has at least one second snap-fit retention feature integral with an interior surface of the temporary coping, the at least one second snap-fit retention feature being configured for snap-fit engagement with the at least one first snap-fit retention feature of the abutment, the temporary coping being sized and shaped to hold a temporary tooth restoration in a patient's mouth to provide tooth function at a location of the dental implant.

2. The system of claim 1, further comprising:
an analog comprising a component supporting portion that comprises at least one third snap-fit retention feature disposed on an outer peripheral surface; and
at least one burnout coping comprising at least one fourth snap-fit retention feature configured for snap-fit engagement with the at least one third retention feature on the analog.

3. The system of claim 2, wherein the component supporting portion of the analog has substantially the same dimensions as the component supporting portion of the abutment.

4. The system of claim 1, further comprising:
an impression coping comprising at least one third snap-fit retention feature configured for snap-fit engagement with the at least one first snap-fit retention feature.

5. The system of claim 1, wherein the at least one first snap-fit retention feature is disposed proximate the implant engaging portion.

6. The system of claim 1, wherein the at least one first snap-fit retention feature comprises at least one retention groove.

7. The system of claim 6, wherein the at least one retention groove extends in a direction substantially transverse to a longitudinal axis of the abutment.

8. The system of claim 6, wherein the at least one retention groove comprises a continuous retention ring around the outer peripheral surface of the component supporting portion, and
wherein the at least one second snap-fit retention feature comprises at least one continuous protrusion ring configured for snap-fit engagement with the retention groove.

9. The system of claim 6, wherein the at least one retention groove comprises a plurality of retention grooves spaced from one another, the plurality of retention grooves being disposed at substantially the same axial location along a length of the abutment, and
wherein the at least one second snap-fit retention feature comprises a plurality of protrusions configured for engagement with the plurality of retention grooves.

10. The system of claim 6, wherein the at least one retention groove has a radiused surface profile with a radius of curvature ranging from about 0.01 in to about 0.06 in.

11. The system of claim 10, wherein the at least one second snap-fit retention feature comprises at least one protrusion feature having a substantially convex surface profile with a radius of curvature ranging from about 0.015 in. to about 0.025 in.

12. The system of claim 6, wherein the at least one retention groove has a depth ranging from about 0.001 in. to about 0.006 in.

13. The system of claim 12, wherein the at least one second snap-fit retention feature comprises at least one protrusion feature protruding from the interior surface of the temporary coping from about 0.002 in. to about 0.006 in.

14. The system of claim 13, wherein the at least one protrusion feature has a height ranging from about 0.015 in. to about 0.040 in., wherein the height is measured along a longitudinal axis of the temporary coping.

15. The system of claim 6, wherein the at least one second snap-fit retention feature is a snap-fit protrusion feature.

16. A system of claim 1, wherein, when the implant engaging portion of the abutment is in mating engagement with the opening of an implant, the temporary coping comprises an apical end that is configured to rest on a shoulder of the implant when the temporary coping is in snap-fit engagement with the abutment.

17. The system of claim 16, wherein an interior surface of the temporary coping tapers from the apical end of the coping toward a coronal end of the temporary coping, a degree of taper of the interior surface substantially corresponding to a degree of taper of the component supporting portion of the abutment.

18. The system of claim 17, wherein the degree of taper of the interior surface ranges from about 4 degrees to about 8 degrees.

19. The system of claim 1, wherein the material is a bis-acrylic material or a bis-acrylic composite material.

20. The system of claim 1, wherein the component supporting portion of the abutment comprises at least one flat external surface portion extending substantially along a length of the component supporting portion, and wherein the temporary coping comprises a flat internal surface portion configured to mate in a substantially flush manner with the at least one flat external surface portion.

21. The system of claim 1, wherein the at least one first snap-fit retention feature and the at least one second snap-fit retention feature are configured to be placed in snap-fit engagement using a force ranging from about 2.5 lb. to about 7 lb.

22. The system of claim 1, wherein the snap-fit engagement between the at least one first snap-fit retention feature and the at least one second snap-fit retention feature is configured to withstand a pull-off force of up to about 20 lb.

23. The system of claim 1, wherein the at least one first snap-fit retention feature is at least one groove and the at least one second snap-fit retention feature is at least one protrusion, and wherein the at least one groove and the at least one protrusion are configured to have a substantially 100 percent interference mating fit when in snap-fit engagement.

24. The system of claim 1, wherein the temporary coping comprises a body having an interior recess with a closed coronal end and an open apical end, the at least one second snap-fit retention feature being positioned closer to the open apical end of the interior recess than the closed coronal end of the interior recess.

25. The system of claim 1, wherein the implant engaging portion is elongated along a longitudinal axis of the abutment.

26. The system of claim 25, wherein the implant engaging portion comprises a post.

27. The system of claim 1, wherein the implant engaging portion comprises a region that tapers in an apical direction.

28. The system of claim 1, wherein the implant engaging portion comprises a frustoconical region configured to be received in mating engagement within an opening in a coronal neck of the implant.

29. The system of claim 1, wherein the implant engaging portion comprises a frustoconical region and a post, wherein the post extends apically relative to the frustoconical region.

30. The system of claim 1, wherein the external surface feature comprises screw threading.

31. The system of claim 1, wherein the abutment further comprises a gingival cuff disposed between the implant engaging portion and the component supporting portion.

32. The system of claim 1, wherein the abutment further comprises a screw-threaded member for threaded engagement of the abutment with the implant.

33. The system of claim 1, wherein the temporary coping further comprises a cuff disposed at an apical end of the temporary coping, the cuff comprising an angled outer surface that flares laterally outwardly relative to the apical end of the temporary coping.

34. A system for dental restorations, the system comprising:
  an abutment comprising an implant engaging portion and a component supporting portion terminating in a coronal end of the abutment,
    wherein the implant engaging portion and the component supporting portion are a single-piece structure,
    wherein the implant engaging portion extends apically from the component supporting portion and has an external surface feature configured to be received in mating engagement within an opening in a dental implant, and
    wherein the component supporting portion comprises at least one first snap-fit retention feature disposed on an outer peripheral surface of the component supporting portion, the at least one first snap-fit retention feature being located at an axial location along the component supporting portion proximate to a location where the implant engaging portion meets the component supporting portion;
  a temporary coping having a frustoconical shape,
    wherein the temporary coping comprises at least one second snap-fit retention feature configured for snap-fit engagement with the at least one first snap-fit retention feature of the abutment, the temporary coping being sized and shaped to hold a temporary tooth restoration in a patient's mouth to provide tooth function at a location of the dental implant; and
  a temporary tooth restoration, wherein the temporary coping is chemically bonded with a veneering material of the temporary tooth restoration.

* * * * *